United States Patent
Park et al.

(10) Patent No.: US 9,808,262 B2
(45) Date of Patent: Nov. 7, 2017

(54) ARTHROPLASTY DEVICES AND RELATED METHODS

(75) Inventors: Ilwhan Park, Walnut Creek, CA (US); Charlie W. Chi, Milpitas, CA (US)

(73) Assignee: Howmedica Osteonics Corporation, Mahwah, NJ (US)

(*) Notice: Subject to any disclaimer, the term of this patent is extended or adjusted under 35 U.S.C. 154(b) by 1810 days.

(21) Appl. No.: 11/642,385

(22) Filed: Dec. 19, 2006

(65) Prior Publication Data

US 2007/0233141 A1    Oct. 4, 2007

Related U.S. Application Data

(60) Provisional application No. 60/773,491, filed on Feb. 15, 2006.

(51) Int. Cl.
  *A61B 17/58* (2006.01)
  *A61B 17/15* (2006.01)
  (Continued)

(52) U.S. Cl.
  CPC .......... *A61B 17/154* (2013.01); *A61B 17/155* (2013.01); *A61B 17/157* (2013.01);
  (Continued)

(58) Field of Classification Search
  CPC .... A61B 17/154; A61B 17/155; A61B 17/157
  (Continued)

(56) References Cited

U.S. PATENT DOCUMENTS

| 3,195,411 A | 7/1965 | MacDonald et al. |
| 3,825,151 A * | 7/1974 | Arnaud .......... 220/742 |

(Continued)

FOREIGN PATENT DOCUMENTS

| DE | 3305237 | 2/1983 |
| DE | 4341367 C1 | 6/1995 |

(Continued)

OTHER PUBLICATIONS

International Search Report and Written Opinion, International Patent Application No. PCT/US2008/083125, dated Mar. 9, 2009, 13 pages.

(Continued)

*Primary Examiner* — Christian Sevilla
(74) *Attorney, Agent, or Firm* — Polsinelli PC

(57) ABSTRACT

Arthroplasty jigs and related methods are disclosed. Some of the arthroplasty jigs may comprise a jig body that is configured to align with a surface of a bone, and a positioning component. Certain of the methods may comprise providing such an arthroplasty jig, and aligning the jig body with a surface of a bone so that the positioning component provides at least one of a visible, audible, or tactile indication that such alignment has been achieved. Some of the arthroplasty jigs may comprise a jig body that is configured to align with a surface of a bone, and that is marked with identifying information. Certain of the methods may comprise providing an arthroplasty jig comprising a jig body that is configured to align with a surface of a bone, or providing an arthroplasty jig blank, and marking the arthroplasty jig or the arthroplasty jig blank with identifying information.

17 Claims, 21 Drawing Sheets

(51) Int. Cl.
*A61B 17/17* (2006.01)
*A61B 90/94* (2016.01)
*A61B 90/00* (2016.01)

(52) U.S. Cl.
CPC .......... *A61B 17/1764* (2013.01); *A61B 90/94* (2016.02); *A61B 17/1739* (2013.01); *A61B 17/1742* (2013.01); *A61B 17/1778* (2016.11); *A61B 90/06* (2016.02); *A61B 2090/036* (2016.02); *A61B 2090/068* (2016.02)

(58) Field of Classification Search
USPC .................................................... 606/87, 88
See application file for complete search history.

(56) References Cited

U.S. PATENT DOCUMENTS

| | | |
|---|---|---|
| D245,920 S | 9/1977 | Shen |
| 4,198,712 A | 4/1980 | Swanson |
| 4,298,992 A | 11/1981 | Burstein |
| 4,436,684 A | 3/1984 | White |
| D274,093 S | 5/1984 | Kenna |
| D274,161 S | 6/1984 | Kenna |
| 4,467,801 A | 8/1984 | Whiteside |
| 4,517,969 A * | 5/1985 | Halcomb et al. ............. 606/102 |
| 4,575,330 A | 3/1986 | Hull |
| 4,646,726 A | 3/1987 | Westin et al. |
| 4,719,585 A | 1/1988 | Cline et al. |
| 4,721,104 A | 1/1988 | Kaufman et al. |
| 4,821,213 A | 4/1989 | Cline et al. |
| 4,822,365 A | 4/1989 | Walker et al. |
| 4,825,857 A | 5/1989 | Kenna |
| 4,841,975 A | 6/1989 | Woolson |
| 4,931,056 A | 6/1990 | Ghajar et al. |
| 4,936,862 A | 6/1990 | Walker et al. |
| 4,976,737 A | 12/1990 | Leake |
| 5,007,936 A | 4/1991 | Woolson |
| 5,011,405 A | 4/1991 | Lemchen |
| 5,027,281 A | 6/1991 | Rekow et al. |
| 5,030,219 A | 7/1991 | Matsen, III et al. |
| 5,035,699 A * | 7/1991 | Coates ........................ 606/86 R |
| 5,037,424 A | 8/1991 | Aboczsky |
| 5,075,866 A | 12/1991 | Goto et al. |
| 5,078,719 A * | 1/1992 | Schreiber ........................ 606/87 |
| 5,086,401 A | 2/1992 | Glassman et al. |
| 5,098,383 A | 3/1992 | Hemmy et al. |
| 5,098,436 A | 3/1992 | Ferrante et al. |
| 5,099,846 A | 3/1992 | Hardy |
| 5,122,144 A | 6/1992 | Bert et al. |
| 5,123,927 A | 6/1992 | Duncan et al. |
| 5,139,419 A | 8/1992 | Andreiko et al. |
| 5,140,646 A | 8/1992 | Ueda |
| 5,141,512 A | 8/1992 | Farmer et al. |
| 5,154,717 A | 10/1992 | Matsen, III et al. |
| 5,156,777 A | 10/1992 | Kaye |
| 5,171,276 A | 12/1992 | Caspari et al. |
| D336,518 S | 6/1993 | Taylor |
| 5,218,427 A | 6/1993 | Koch |
| 5,234,433 A | 8/1993 | Bert et al. |
| 5,236,461 A | 8/1993 | Forte |
| 5,274,565 A | 12/1993 | Reuben |
| 5,282,803 A * | 2/1994 | Lackey ........................ 606/80 |
| 5,298,115 A | 3/1994 | Leonard |
| 5,298,254 A | 3/1994 | Prewett et al. |
| 5,305,203 A | 4/1994 | Raab |
| D346,979 S | 5/1994 | Stalcup et al. |
| 5,320,529 A | 6/1994 | Pompa |
| 5,360,446 A | 11/1994 | Kennedy |
| 5,364,402 A * | 11/1994 | Mumme et al. ............... 606/88 |
| 5,365,996 A | 11/1994 | Crook |
| 5,368,478 A | 11/1994 | Andreiko et al. |
| D355,254 S | 2/1995 | Krafft et al. |
| D357,315 S | 4/1995 | Dietz |
| 5,408,409 A | 4/1995 | Glassman et al. |
| 5,431,562 A | 7/1995 | Andreiko et al. |
| 5,448,489 A | 9/1995 | Reuben |
| 5,452,407 A | 9/1995 | Crook |
| 5,462,550 A | 10/1995 | Dietz et al. |
| 5,484,446 A | 1/1996 | Burke et al. |
| D372,309 S | 7/1996 | Heldreth |
| D374,078 S | 9/1996 | Johnson et al. |
| 5,556,278 A | 9/1996 | Meitner |
| 5,569,260 A | 10/1996 | Petersen |
| 5,569,261 A * | 10/1996 | Marik et al. ..................... 606/88 |
| 5,601,563 A | 2/1997 | Burke et al. |
| 5,601,565 A | 2/1997 | Huebner |
| 5,662,656 A | 9/1997 | White |
| 5,681,354 A | 10/1997 | Eckhoff |
| 5,682,886 A | 11/1997 | Delp et al. |
| 5,683,398 A * | 11/1997 | Carls et al. ..................... 606/89 |
| 5,690,635 A | 11/1997 | Matsen, III et al. |
| 5,716,361 A | 2/1998 | Masini |
| 5,725,376 A | 3/1998 | Poirier |
| 5,735,277 A | 4/1998 | Schuster |
| 5,741,215 A | 4/1998 | D'Urso |
| 5,749,876 A | 5/1998 | Duvillier et al. |
| 5,755,803 A * | 5/1998 | Haines et al. ............. 623/20.14 |
| 5,768,134 A | 6/1998 | Swaelens |
| 5,769,092 A | 6/1998 | Williamson, Jr. |
| 5,769,859 A * | 6/1998 | Dorsey ........................ 606/119 |
| D398,058 S | 9/1998 | Collier |
| 5,810,830 A | 9/1998 | Noble et al. |
| 5,824,085 A | 10/1998 | Sahay et al. |
| 5,824,098 A | 10/1998 | Stein |
| 5,824,100 A | 10/1998 | Kester et al. |
| 5,860,980 A | 1/1999 | Axelson, Jr. et al. |
| 5,860,981 A * | 1/1999 | Bertin et al. ..................... 606/89 |
| 5,871,018 A | 2/1999 | Delp et al. |
| 5,880,976 A | 3/1999 | DiGioia, III et al. |
| 5,908,424 A | 6/1999 | Bertin et al. |
| 5,911,724 A | 6/1999 | Wehrli |
| 5,916,221 A | 6/1999 | Hodorek et al. |
| 5,964,808 A | 10/1999 | Blaha et al. |
| 5,967,777 A | 10/1999 | Klein et al. |
| 5,993,448 A | 11/1999 | Remmler |
| 5,995,738 A | 11/1999 | DiGioia, III et al. |
| 6,002,859 A | 12/1999 | DiGioia, III et al. |
| 6,068,658 A | 5/2000 | Insall et al. |
| 6,090,114 A | 7/2000 | Matsuno et al. |
| 6,096,043 A | 8/2000 | Techiera et al. |
| 6,106,529 A | 8/2000 | Techiera |
| 6,112,109 A | 8/2000 | D'Urso |
| 6,126,690 A | 10/2000 | Ateshian et al. |
| 6,132,447 A * | 10/2000 | Dorsey ........................ 606/174 |
| 6,161,080 A | 12/2000 | Aouni-Ateshian et al. |
| 6,171,340 B1 | 1/2001 | McDowell |
| 6,173,200 B1 | 1/2001 | Cooke et al. |
| 6,183,515 B1 | 2/2001 | Barlow et al. |
| 6,205,411 B1 | 3/2001 | DiGioia, III et al. |
| 6,228,121 B1 | 5/2001 | Khalili |
| 6,254,639 B1 | 7/2001 | Peckitt |
| 6,285,902 B1 | 9/2001 | Kienzle, III et al. |
| 6,327,491 B1 | 12/2001 | Franklin et al. |
| 6,343,987 B2 | 2/2002 | Hayama et al. |
| 6,382,975 B1 | 5/2002 | Poirier |
| 6,383,228 B1 | 5/2002 | Schmotzer |
| 6,385,475 B1 | 5/2002 | Cinquin et al. |
| 6,415,171 B1 | 7/2002 | Gueziec et al. |
| 6,458,135 B1 * | 10/2002 | Harwin et al. ................. 606/88 |
| 6,503,254 B2 | 1/2003 | Masini |
| 6,510,334 B1 | 1/2003 | Schuster et al. |
| 6,514,259 B2 | 2/2003 | Picard et al. |
| 6,520,964 B2 | 2/2003 | Tallarida et al. |
| 6,533,737 B1 | 3/2003 | Brosseau et al. |
| D473,307 S | 4/2003 | Cooke |
| 6,540,784 B2 | 4/2003 | Barlow et al. |
| 6,558,426 B1 | 5/2003 | Masini |
| 6,575,980 B1 * | 6/2003 | Robie et al. ..................... 606/88 |
| 6,602,259 B1 | 8/2003 | Masini |
| 6,672,870 B2 | 1/2004 | Knapp |
| 6,692,448 B2 | 2/2004 | Tanaka et al. |
| 6,701,174 B1 | 3/2004 | Krause et al. |
| 6,702,821 B2 | 3/2004 | Bonutti |
| 6,711,431 B2 | 3/2004 | Sarin et al. |

(56) References Cited

U.S. PATENT DOCUMENTS

| | | |
|---|---|---|
| 6,711,432 B1 | 3/2004 | Krause et al. |
| 6,712,856 B1 | 3/2004 | Carignan et al. |
| 6,716,249 B2 | 4/2004 | Hyde |
| 6,738,657 B1 | 5/2004 | Franklin et al. |
| 6,747,646 B2 | 6/2004 | Gueziec et al. |
| 6,770,099 B2 | 8/2004 | Andriacchi et al. |
| 6,799,066 B2 | 9/2004 | Steines et al. |
| 6,814,575 B2 | 11/2004 | Poirier |
| 6,905,510 B2 | 6/2005 | Saab |
| 6,905,514 B2 | 6/2005 | Carignan et al. |
| 6,923,817 B2 | 8/2005 | Carson et al. |
| 6,932,842 B1 | 8/2005 | Litschko et al. |
| 6,944,518 B2 | 9/2005 | Roose |
| 6,955,345 B2 | 10/2005 | Kato |
| 6,969,393 B2 | 11/2005 | Pinczewski et al. |
| 6,975,894 B2 | 12/2005 | Wehrli et al. |
| 6,978,188 B1 | 12/2005 | Christensen |
| 7,029,479 B2 | 4/2006 | Tallarida et al. |
| 7,033,360 B2 | 4/2006 | Cinquin et al. |
| 7,039,225 B2 | 5/2006 | Tanaka et al. |
| 7,060,074 B2 | 6/2006 | Rosa et al. |
| 7,074,241 B2 | 7/2006 | McKinnon |
| 7,090,677 B2 | 8/2006 | Fallin et al. |
| 7,094,241 B2 | 8/2006 | Hodorek et al. |
| RE39,301 E | 9/2006 | Bertin |
| 7,104,997 B2 | 9/2006 | Lionberger et al. |
| 7,128,745 B2 | 10/2006 | Masini et al. |
| D532,515 S | 11/2006 | Buttler et al. |
| 7,141,053 B2 | 11/2006 | Rose et al. |
| 7,153,309 B2 | 12/2006 | Huebner et al. |
| 7,166,833 B2 | 1/2007 | Smith |
| 7,172,597 B2 | 2/2007 | Sanford |
| 7,174,282 B2 | 2/2007 | Hollister et al. |
| 7,177,386 B2 | 2/2007 | Mostafavi et al. |
| 7,184,814 B2 | 2/2007 | Lang et al. |
| 7,235,080 B2 | 6/2007 | Hodorek |
| 7,238,190 B2 | 7/2007 | Schon et al. |
| 7,239,908 B1 | 7/2007 | Alexander et al. |
| 7,258,701 B2 | 8/2007 | Aram et al. |
| 7,275,218 B2 | 9/2007 | Petrella et al. |
| 7,309,339 B2 | 12/2007 | Cusick et al. |
| 7,359,746 B2 | 4/2008 | Arata |
| 7,383,164 B2 | 6/2008 | Aram et al. |
| 7,388,972 B2 | 6/2008 | Kitson |
| 7,393,012 B2 | 7/2008 | Funakura et al. |
| 7,394,946 B2 | 7/2008 | Dewaele |
| 7,429,346 B2 | 9/2008 | Ensign et al. |
| 7,468,075 B2 | 12/2008 | Lang et al. |
| 7,547,307 B2 | 6/2009 | Carson et al. |
| 7,611,519 B2 | 11/2009 | Lefevre et al. |
| 7,616,800 B2 | 11/2009 | Paik et al. |
| 7,618,421 B2 | 11/2009 | Axelson, Jr. et al. |
| 7,618,451 B2 | 11/2009 | Berez et al. |
| 7,630,750 B2 | 12/2009 | Liang et al. |
| 7,634,119 B2 | 12/2009 | Tsougarakis et al. |
| 7,634,306 B2 | 12/2009 | Sarin et al. |
| 7,641,660 B2 | 1/2010 | Lakin et al. |
| 7,643,862 B2 | 1/2010 | Schoenefeld |
| 7,660,623 B2 | 2/2010 | Hunter et al. |
| 7,693,321 B2 | 4/2010 | Lehtonen-Krause |
| 7,702,380 B1 | 4/2010 | Dean |
| 7,715,602 B2 | 5/2010 | Richard |
| 7,717,956 B2 | 5/2010 | Lang |
| D618,796 S | 6/2010 | Cantu et al. |
| 7,747,305 B2 | 6/2010 | Dean et al. |
| D619,718 S | 7/2010 | Gannoe et al. |
| D622,854 S | 8/2010 | Otto et al. |
| 7,787,932 B2 | 8/2010 | Vilsmeier et al. |
| 7,794,467 B2 | 9/2010 | McGinley et al. |
| D626,234 S | 10/2010 | Otto et al. |
| 7,806,896 B1 | 10/2010 | Bonutti |
| 7,842,039 B2 | 11/2010 | Hodorek et al. |
| 7,842,092 B2 | 11/2010 | Otto et al. |
| 7,881,768 B2 | 2/2011 | Lang et al. |
| 7,894,650 B2 | 2/2011 | Weng et al. |
| 7,927,335 B2 | 4/2011 | Deffenbaugh et al. |
| 7,940,974 B2 | 5/2011 | Skinner et al. |
| 7,950,924 B2 | 5/2011 | Brajnovic |
| 7,963,968 B2 | 6/2011 | Dees, Jr. |
| D642,263 S | 7/2011 | Park |
| 8,007,448 B2 | 8/2011 | Moctezuma de La Barrera |
| 8,036,729 B2 | 10/2011 | Lang et al. |
| 8,059,878 B2 | 11/2011 | Feilkas et al. |
| 8,077,950 B2 | 12/2011 | Tsougarakis et al. |
| 8,086,336 B2 | 12/2011 | Christensen |
| 8,115,485 B1 | 2/2012 | Maier et al. |
| 8,126,533 B2 | 2/2012 | Lavallee |
| RE43,282 E | 3/2012 | Alexander et al. |
| 8,133,234 B2 | 3/2012 | Meridew et al. |
| 8,142,189 B2 | 3/2012 | Brajnovic |
| 8,160,345 B2 | 4/2012 | Pavlovskaia et al. |
| 8,170,716 B2 | 5/2012 | Coste-Maniere et al. |
| 8,177,850 B2 | 5/2012 | Rudan et al. |
| 8,202,324 B2 | 6/2012 | Meulink et al. |
| 8,214,016 B2 | 7/2012 | Lavallee et al. |
| 8,221,430 B2 | 7/2012 | Park et al. |
| 8,231,634 B2 | 7/2012 | Mahfouz et al. |
| 8,234,097 B2 | 7/2012 | Steines et al. |
| 8,241,293 B2 | 8/2012 | Stone et al. |
| 8,306,601 B2 | 11/2012 | Lang et al. |
| 8,311,306 B2 | 11/2012 | Pavlovskaia et al. |
| 8,337,501 B2 | 12/2012 | Fitz et al. |
| 8,460,302 B2 | 6/2013 | Park et al. |
| 2002/0055783 A1 | 5/2002 | Tallarida et al. |
| 2002/0087274 A1 | 7/2002 | Alexander et al. |
| 2002/0160337 A1 | 10/2002 | Klein et al. |
| 2003/0009167 A1 | 1/2003 | Wozencroft |
| 2003/0055502 A1 | 3/2003 | Lang et al. |
| 2003/0176783 A1 | 9/2003 | Hu |
| 2003/0216669 A1 | 11/2003 | Lang et al. |
| 2004/0097952 A1 | 5/2004 | Sarin et al. |
| 2004/0102792 A1 | 5/2004 | Sarin et al. |
| 2004/0102866 A1 | 5/2004 | Harris et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153066 A1 | 8/2004 | Coon et al. |
| 2004/0153079 A1 | 8/2004 | Tsougarakis et al. |
| 2004/0153087 A1 | 8/2004 | Sanford et al. |
| 2004/0171924 A1 | 9/2004 | Mire et al. |
| 2004/0204760 A1 | 10/2004 | Fitz et al. |
| 2004/0220583 A1 | 11/2004 | Pieczynski, II et al. |
| 2004/0236424 A1* | 11/2004 | Berez et al. ............... 623/14.12 |
| 2004/0243148 A1 | 12/2004 | Wasielewski |
| 2004/0243481 A1 | 12/2004 | Bradbury et al. |
| 2004/0254584 A1 | 12/2004 | Sarin et al. |
| 2004/0260301 A1* | 12/2004 | Lionberger et al. ............ 606/88 |
| 2005/0054914 A1 | 3/2005 | Duerk et al. |
| 2005/0059978 A1 | 3/2005 | Sherry et al. |
| 2005/0065617 A1 | 3/2005 | Moctezuma de la Barrera |
| 2005/0080426 A1 | 4/2005 | Qian |
| 2005/0096535 A1 | 5/2005 | Moctezuma de la Barrera |
| 2005/0113841 A1 | 5/2005 | Sheldon et al. |
| 2005/0119664 A1 | 6/2005 | Carignan et al. |
| 2005/0148843 A1* | 7/2005 | Roose ......................... 600/407 |
| 2005/0148860 A1 | 7/2005 | Liew et al. |
| 2005/0149091 A1* | 7/2005 | Tanamal et al. ............. 606/184 |
| 2005/0192588 A1 | 9/2005 | Garcia |
| 2005/0216024 A1 | 9/2005 | Massoud |
| 2005/0234461 A1* | 10/2005 | Burdulis et al. ................ 606/79 |
| 2005/0245934 A1 | 11/2005 | Tuke et al. |
| 2005/0245936 A1 | 11/2005 | Tuke et al. |
| 2005/0256389 A1 | 11/2005 | Koga et al. |
| 2005/0267584 A1 | 12/2005 | Burdulis, Jr. et al. |
| 2005/0272998 A1 | 12/2005 | Diehl et al. |
| 2006/0015018 A1 | 1/2006 | Jutras et al. |
| 2006/0015030 A1 | 1/2006 | Poulin et al. |
| 2006/0015109 A1 | 1/2006 | Haines |
| 2006/0015188 A1 | 1/2006 | Grimes |
| 2006/0030853 A1 | 2/2006 | Haines |
| 2006/0036257 A1 | 2/2006 | Steffensmeier |
| 2006/0079755 A1 | 4/2006 | Stazzone et al. |
| 2006/0110017 A1 | 5/2006 | Tsai et al. |
| 2006/0111628 A1 | 5/2006 | Tsai et al. |

(56) References Cited

U.S. PATENT DOCUMENTS

| | | |
|---|---|---|
| 2006/0122491 A1 | 6/2006 | Murray et al. |
| 2006/0155293 A1 | 7/2006 | McGinley et al. |
| 2006/0155294 A1 | 7/2006 | Steffensmeier et al. |
| 2006/0195113 A1 | 8/2006 | Masini |
| 2006/0244448 A1 | 11/2006 | Ballon et al. |
| 2006/0271058 A1 | 11/2006 | Ashton et al. |
| 2006/0293681 A1 | 12/2006 | Claypool et al. |
| 2007/0005073 A1 | 1/2007 | Claypool et al. |
| 2007/0010732 A1 | 1/2007 | DeYoe et al. |
| 2007/0021838 A1 | 1/2007 | Dugas et al. |
| 2007/0038059 A1 | 2/2007 | Sheffer et al. |
| 2007/0055268 A1 | 3/2007 | Utz et al. |
| 2007/0073305 A1 | 3/2007 | Lionberger et al. |
| 2007/0083266 A1 | 4/2007 | Lang |
| 2007/0100338 A1 | 5/2007 | Deffenbaugh et al. |
| 2007/0100462 A1 | 5/2007 | Lang et al. |
| 2007/0106389 A1 | 5/2007 | Croxton et al. |
| 2007/0114370 A1 | 5/2007 | Smith et al. |
| 2007/0118055 A1 | 5/2007 | McCombs |
| 2007/0118243 A1 | 5/2007 | Schroeder et al. |
| 2007/0123856 A1 | 5/2007 | Deffenbaugh et al. |
| 2007/0123857 A1 | 5/2007 | Deffenbaugh et al. |
| 2007/0123912 A1 | 5/2007 | Carson |
| 2007/0162039 A1 | 7/2007 | Wozencroft |
| 2007/0167833 A1 | 7/2007 | Redel et al. |
| 2007/0173858 A1 | 7/2007 | Engh et al. |
| 2007/0191741 A1 | 8/2007 | Tsai et al. |
| 2007/0198022 A1 | 8/2007 | Lang et al. |
| 2007/0213738 A1 | 9/2007 | Martin et al. |
| 2007/0219560 A1 | 9/2007 | Hodorek |
| 2007/0226986 A1 | 10/2007 | Chi et al. |
| 2007/0232959 A1 | 10/2007 | Couture et al. |
| 2007/0233136 A1 | 10/2007 | Wozencroft |
| 2007/0233140 A1 | 10/2007 | Metzger et al. |
| 2007/0233269 A1 | 10/2007 | Steines et al. |
| 2007/0239167 A1 | 10/2007 | Pinczewski et al. |
| 2007/0249967 A1 | 10/2007 | Buly et al. |
| 2007/0276224 A1 | 11/2007 | Lang et al. |
| 2007/0276400 A1 | 11/2007 | Moore et al. |
| 2007/0282451 A1 | 12/2007 | Metzger et al. |
| 2007/0288030 A1 | 12/2007 | Metzger et al. |
| 2008/0004701 A1 | 1/2008 | Axelson et al. |
| 2008/0015433 A1 | 1/2008 | Alexander et al. |
| 2008/0015599 A1 | 1/2008 | D'Alessio et al. |
| 2008/0015600 A1 | 1/2008 | D'Alessio et al. |
| 2008/0015602 A1 | 1/2008 | Axelson et al. |
| 2008/0015606 A1 | 1/2008 | D'Alessio et al. |
| 2008/0015607 A1 | 1/2008 | D'Alessio et al. |
| 2008/0021299 A1 | 1/2008 | Meulink |
| 2008/0031412 A1 | 2/2008 | Lang et al. |
| 2008/0033442 A1 | 2/2008 | Amiot et al. |
| 2008/0058613 A1 | 3/2008 | Lang et al. |
| 2008/0088761 A1 | 4/2008 | Lin et al. |
| 2008/0089591 A1 | 4/2008 | Zhou et al. |
| 2008/0114370 A1 | 5/2008 | Schoenefeld |
| 2008/0147072 A1 | 6/2008 | Park et al. |
| 2008/0153067 A1 | 6/2008 | Berckmans et al. |
| 2008/0161815 A1 | 7/2008 | Schoenefeld et al. |
| 2008/0195108 A1 | 8/2008 | Bhatnagar et al. |
| 2008/0215059 A1 | 9/2008 | Carignan et al. |
| 2008/0234685 A1 | 9/2008 | Gjerde |
| 2008/0243127 A1 | 10/2008 | Lang et al. |
| 2008/0257363 A1 | 10/2008 | Schoenefeld et al. |
| 2008/0262624 A1 | 10/2008 | White et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0286722 A1 | 11/2008 | Berckmans, III et al. |
| 2008/0287953 A1 | 11/2008 | Sers |
| 2008/0287954 A1 | 11/2008 | Kunz et al. |
| 2008/0312659 A1 | 12/2008 | Metzger et al. |
| 2008/0319491 A1 | 12/2008 | Schoenefeld |
| 2009/0024131 A1 | 1/2009 | Metzger et al. |
| 2009/0085567 A1 | 4/2009 | Kimmlingen et al. |
| 2009/0088763 A1 | 4/2009 | Aram et al. |
| 2009/0089034 A1 | 4/2009 | Penney et al. |
| 2009/0093816 A1 | 4/2009 | Roose et al. |
| 2009/0110498 A1 | 4/2009 | Park |
| 2009/0112213 A1 | 4/2009 | Heavener et al. |
| 2009/0131941 A1 | 5/2009 | Park et al. |
| 2009/0138020 A1 | 5/2009 | Park et al. |
| 2009/0151736 A1 | 6/2009 | Belcher et al. |
| 2009/0157083 A1 | 6/2009 | Park et al. |
| 2009/0163923 A1 | 6/2009 | Flett et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0234217 A1 | 9/2009 | Mire et al. |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0087829 A1 | 4/2010 | Metzger et al. |
| 2010/0152741 A1 | 6/2010 | Park et al. |
| 2010/0160917 A1 | 6/2010 | Fitz et al. |
| 2010/0168754 A1 | 7/2010 | Fitz et al. |
| 2010/0174376 A1 | 7/2010 | Lang |
| 2010/0191242 A1 | 7/2010 | Massoud |
| 2010/0198351 A1 | 8/2010 | Meulink |
| 2010/0228257 A1 | 9/2010 | Bonutti |
| 2010/0256479 A1 | 10/2010 | Park et al. |
| 2010/0274534 A1 | 10/2010 | Steines et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0029093 A1 | 2/2011 | Bojarski et al. |
| 2011/0046735 A1 | 2/2011 | Metzger et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071537 A1 | 3/2011 | Koga et al. |
| 2011/0071581 A1 | 3/2011 | Lang et al. |
| 2011/0087332 A1 | 4/2011 | Bojarski et al. |
| 2011/0092804 A1 | 4/2011 | Schoenefeld et al. |
| 2011/0092978 A1 | 4/2011 | McCombs |
| 2011/0144760 A1 | 6/2011 | Wong et al. |
| 2011/0160736 A1 | 6/2011 | Meridew et al. |
| 2011/0166578 A1 | 7/2011 | Stone et al. |
| 2011/0166666 A1 | 7/2011 | Meulink et al. |
| 2011/0172672 A1 | 7/2011 | Dubeau et al. |
| 2011/0190899 A1 | 8/2011 | Pierce et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0268248 A1 | 11/2011 | Simon et al. |
| 2011/0270072 A9 | 11/2011 | Feilkas et al. |
| 2011/0276145 A1 | 11/2011 | Carignan et al. |
| 2011/0282473 A1 | 11/2011 | Pavlovskaia et al. |

(56) References Cited

U.S. PATENT DOCUMENTS

| | | |
|---|---|---|
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0029520 A1 | 2/2012 | Lang et al. |
| 2012/0041446 A1 | 2/2012 | Wong et al. |
| 2012/0053591 A1 | 3/2012 | Haines et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0093377 A1 | 4/2012 | Tsougarakis et al. |
| 2012/0101503 A1 | 4/2012 | Lang et al. |
| 2012/0143197 A1 | 6/2012 | Lang et al. |
| 2012/0150243 A9 | 6/2012 | Crawford et al. |
| 2012/0151730 A1 | 6/2012 | Fitz et al. |
| 2012/0158001 A1 | 6/2012 | Burdulis, Jr. et al. |
| 2012/0158002 A1 | 6/2012 | Carignan et al. |
| 2012/0165821 A1 | 6/2012 | Carignan et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0215226 A1 | 8/2012 | Bonutti |
| 2012/0230566 A1 | 9/2012 | Dean et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski et al. |
| 2012/0265499 A1 | 10/2012 | Mahfouz et al. |
| 2012/0310400 A1 | 12/2012 | Park |
| 2013/0116697 A1 | 5/2013 | Park et al. |
| 2013/0190767 A1 | 7/2013 | Park et al. |
| 2013/0345845 A1 | 12/2013 | Park et al. |
| 2014/0005997 A1 | 1/2014 | Park |

FOREIGN PATENT DOCUMENTS

| | | | |
|---|---|---|---|
| DE | 10 2005 023 028 A1 | 11/2006 | |
| EP | 0097001 A | 12/1983 | |
| EP | 0574098 A | 12/1993 | |
| EP | 0622052 A | 11/1994 | |
| EP | 0908836 A2 | 4/1999 | |
| EP | 0908836 A3 | 12/1999 | |
| EP | 1059153 A2 | 12/2000 | |
| EP | 1486900 | 12/2004 | |
| EP | 1 532 939 A1 | 5/2005 | |
| EP | 1669033 A1 * | 6/2006 | ............ A61B 17/15 |
| GB | 2215610 | 9/1989 | |
| GB | 2420717 A | 6/2006 | |
| JP | 10-94538 | 4/1998 | |
| JP | 2001-092950 | 4/2001 | |
| WO | WO-93/25157 A1 | 12/1993 | |
| WO | WO 95/07509 A1 | 3/1995 | |
| WO | WO 95/27450 | 10/1995 | |
| WO | WO 97/23172 A2 | 7/1997 | |
| WO | WO 98/12995 A2 | 4/1998 | |
| WO | WO 9832384 A1 * | 7/1998 | ............ A61B 17/58 |
| WO | WO 00/35346 | 6/2000 | |
| WO | WO-01/00096 A1 | 1/2001 | |
| WO | WO-01/70142 A1 | 9/2001 | |
| WO | WO 01/85040 A1 | 11/2001 | |
| WO | WO 02/96268 A2 | 12/2002 | |
| WO | WO-2004/032806 A1 | 4/2004 | |
| WO | WO-2004/049981 A2 | 6/2004 | |
| WO | WO-2004/049981 A3 | 6/2004 | |
| WO | WO-2005/051240 A1 | 6/2005 | |
| WO | WO 2005/087125 A2 | 9/2005 | |
| WO | WO-2006/058057 A2 | 6/2006 | |
| WO | WO-2006/060795 A1 | 6/2006 | |
| WO | WO-2006/092600 A1 | 9/2006 | |
| WO | WO 2006/134345 A1 | 12/2006 | |
| WO | WO-2007/014164 A2 | 2/2007 | |
| WO | WO 2007/058632 A1 | 5/2007 | |
| WO | WO 2007/092841 A2 | 8/2007 | |
| WO | WO 2007/097853 A2 | 8/2007 | |

OTHER PUBLICATIONS

Akenine-Moller, T. et al. (2002). *Real-Time Rendering, Second Edition.* AK Peters: Natick, MA, six pages (Table of contents).

Berry, E. et al. (2005). "Personalized Image-Based Templates for Intra-Operative Guidance," *Proc. Inst. Mech. Eng Part H: J. Engineering in Medicine* 219:111-118.

Blinn, J. (1996). *Jim Blinn's Corner—A Trip Down the Graphics Pipeline.* Morgan Kaufmann Publishers, Inc.: San Francisco, CA, five pages (Table of Contents).

Chauhan, S.K. et al. (Apr. 2004). "Computer-Assisted Knee Arthroplasty Versus a Conventional Jig-Based Technique, A Randomised, Prospective Trial," *The Journal of Bone and Joint Surgery* 86-B(3):372-377.

Cohen, M.F. et al. (1993). *Radiosity and Realistic Image Synthesis.* Academic Press Professional: Cambridge, MA, eight pages (Table of Contents).

Delp, S.L. et al. (Sep. 1998). "Computer Assisted Knee Replacement," *Clinical Orthopaedics and Related Research* 354:49-56.

Dutre, P. et al. (2003). *Advanced Global Illumination.* AK Peters: Natick, MA, five pages (Table of Contents).

Foley, J.D. et al. (1990). *Computer Graphics Principles and Practice, Second Edition.* Addison-Wesley Publishing Company: Reading, MA, nine pages (Table of Contents).

Glassner, A.S. ed. (1989). *An Introduction to Ray Tracing.* Academic Press Inc.: San Diego, CA, four pages (Table of Contents).

Glassner. A.S. (1995). *Principles of Digital Image Synthesis.* Morgan Kaufmann Publishers, Inc.: San Francisco, CA, thirty-two pages (Table of Contents).

Gooch, B. et al. (2001). *Non-Photorealistic Rendering.* AK Peters: Natick, MA, four pages (Table of Contents).

Hafez, M.A. et al. (Oct. 20-22, 2005). "Patient Specific Instrumentation for TKA: Testing the Reliability Using a Navigational System," *MIS Meets CAOS Symposium & Instructional Academy, Less and Minimally Invasive Surgery for Joint Arthroplasty: Fact and Fiction Syllabus: San Diego, CA,* 8 pages.

Hafez, M.A. et al. (2004). "Computer Assisted Total Knee Replacement: Could a Two-Piece Custom Template Replace the Complex Conventional Instrumentations?" *Computer Aided Surgery* 9(3):93-94.

Hafez, M.A. et al. (2006). "Computer-Assisted Total Knee Arthroplasty Using Patient-Specific Templating," *Clinical Orthopaedics and Related Research* 0:1-9.

Jensen, H.W. (2001). *Realistic Image Synthesis Using Photon Mapping.* AK Peters: Natick, MA, seven pages (Table of Contents).

Kidder, J. et al. (Nov. 21-22, 1996). "3-D Model Acquisition, Design, Planning and Manufacturing of Orthopaedic Devices: A Framework," *In Advanced Sensor and Control-System Interface.* B.O. Nnaji ed., Proceedings SPIE—The International Society for Optical Engineering: Bellingham, WA, pp. 9-22.

Pharr, M. et al. (2004). *Physically Based Rendering, From Theory to Implementation.* Morgan Kaufmann Publishers: San Francisco, CA, thirteen pages (Table of Contents).

Platt, G. et al. (Feb. 1969). "Mould Arthroplasty of the Knee, A Ten-Year Follow-Up Study," *The Journal of Bone and Joint Surgery British* vol. 51-B(1):76-87.

Potter, T.A. (Aug. 1969). "Arthroplasty of the Knee With Tibial Metallic Implants of the McKeever and MacIntosh Design," *The Surgical Clinics of North America* 49(4):903-915.

Radermacher, K. et al. (Sep. 1998). "Computer Assisted Orthopaedic Surgery With Image-Based Individual Templates," *Clinical Orthopaedics and Related Research* 354:28-38.

Shirley, P. et al. (2003). *Realistic Ray Tracing, Second Edition.* AK Peters: Natick, MA, seven pages (Table of Contents).

Strothotte, T. et al. (2002). *Non-Photorealistic Computer Graphics, Modeling, Rendering, and Animation.* Morgan Kaufmann Publishers: San Francisco, CA, nine pages (Table of Contents).

(56) References Cited

OTHER PUBLICATIONS

U.S. Appl. No. 10/146,862, filed May 15, 2002, for Park et al.
Vande Berg, B.C. et al. (Feb. 2002). "Assessment of Knee Cartilage in Cadavers with Dual-Detector Spiral CT Arthrography and MR Imaging," *Radiology* 222(2):430-436.
Wikipedia, the Free Encyclopedia. (Date Unknown). "CNC," located at <http://en.wikipedia.org/wiki/CNC>, last visited on Apr. 12, 2007, 6 pages.
Author Unknown, "MRI Protocol Reference," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for GE Systems," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for Phillips Systems," ConforMIS, Inc., copyright 2007, http://www.conformis.com/Imaging-Professionals/MRI-Protocol-Guides, last visited on Mar. 28, 2008, 19 pages.
Author Unknown, "MRI Protocol Reference Guide for Siemens Systems," ConforMIS, Inc., copyright 2007, http://www.conformis.com/Imaging-Professionals/MRI-Protocol-Guides, last visited on Mar. 28, 2008, 18 pages.
Barequet et al., "Filling Gaps in the Boundary of a Polyhedron," *Computer Aided Geometric Design*, vol. 12, pp. 207-229, 1995.
Barequet et al., "Repairing CAD Models," Proceedings of the 8th IEEE Visualization '97 Conference, pp. 363-370, Oct. 1997.
Biščević et al., "Variations of Femoral Condyle Shape," *Coll. Antropol.*, vol. 29 No. 2, pp. 409-414, 2005.
Bøhn et al., "A Topology-Based Approach for Shell-Closure," *Geometric Modeling for Product Realization* (P.R. Wilson et al. editors), pp. 297-319, Elsevier Science Publishers B.V., North-Holland, 1993.
Couglin et al., "Tibial Axis and Patellar Position Relative to the Femoral Epicondylar Axis During Squatting," *The Journal of Arthroplasty*, vol. 18, No. 8, Elsevier, 2003.
Eckhoff et al., "Three-Dimensional Mechanics, Kinematics, and Morphology of the Knee Viewed in Virtual Realty," *The Journal of Bone and Joint Surgery*, vol. 87-A, Supplement 2, pp. 71-80, 2005.
Erikson, "Error Correction of a Large Architectural Model: The Henderson County Courthouse," Technical Report TR95-013, Dept. of Computer Science, University of North Carolina at Chapel Hill, pp. 1-11, 1995.
Ervin et al., *Landscape Modeling*, McGraw-Hill, New York, NY, 8 pages (Table of Contents), 2001.
Farin, *NURB Curves and Surfaces: From Projective Geometry to Practical Use*, AK Peters, Wellesley, MA, 7 pages (Table of Contents), 1995.
Fleischer et al., "Accurate Polygon Scan Conversion Using Half-Open Intervals," *Graphics Gems III*, pp. 362-365, code: pp. 599-605, 1992.
Grüne et al., "On numerical algorithm and interactive visualization for optimal control problems," *Journal of Computation and Visualization in Science*, vol. 1, No. 4, pp. 221-229, Jul. 1999.
Guéziec et al., "Converting Sets of Polygons to Manifold Surfaces by Cutting and Stitching," Proc. IEEE Visualization 1998, pp. 383-390, Oct. 1998.
Jones et al., "A new approach to the construction of surfaces from contour data," *Computer Graphics Forum*, vol. 13, No. 3, pp. 75-84, 1994 [ISSN 0167-7055].
Khorramabadi, "A Walk Through the Planned CS Building," Technical Report UCB/CSD 91/652, Computer Science Department, University of California at Berkeley, 74 pages, 1991.
Kumar, *Robust Incremental Polygon Triangulation for Surface Rendering*, Center for Geometric Computing, Department of Computer Science, Johns Hopkins University, Baltimore, MD, WSCG, The International Conference in Central Europe on Computer Graphics, Visualization and Computer Vision, pp. 381-388, 2000.

Lorensen et al., "Marching Cubes: A High Resolution 3d Surface Construction Algorithm," *Computer Graphics*, vol. 21, No. 4, pp. 163-169, 1987.
Nooruddin et al., Simplification and Repair of Polygonal Models Using Volumetric Techniques, *IEEE Transactions on Visualization and Computer Graphics*, vol. 9, No. 2, pp. 191-205, Apr.-Jun. 2003.
Rohlfing et al., "*Quo Vadis*, Atlas-Based Segmentation?", *The Handbook of Medical Image Analysis: Segmentation and Registration Models* (Kluwer), pp. 1-55, (http://www.stanford.edu/~rohlfing/publications/2005-rohlfing-chapter-quo_vadis_atlas_based_segmentation.pdf).
Office Action, U.S. Appl. No. 10/146,862, mailed Jan. 13, 2005, 10 pages.
Amendment and Response to Office Action and Petition to Revive, U.S. Appl. No. 10/146,862, filed Jan. 18, 2006, 29 pages.
International Search Report and Written Opinion, PCT/US2007/001624, dated Dec. 12, 2007, 14 pages.
International Search Report and Written Opinion, PCT/US2007/001622, dated Jun. 11, 2007, 14 pages.
Restriction Requirement, U.S. Appl. No. 11/641,569, mailed Apr. 27, 2009, 7 pages.
International Search Report and Written Opinion, International Application No. PCT/US2009/34983, mailed May 22, 2009, 15 pages.
International Search Report and Written Opinion, International Application No. PCT/US2009/034967, mailed Jun. 16, 2009, 15 pages.
International Search Report and Written Opinion, International Application No. PCT/US2009/041519, mailed Jun. 17, 2009, 10 pages.
Kunz et al., "Computer Assisted Hip Resurfacing Using Individualized Drill Templates," The Journal of Arthroplasty, vol. 00, No. 0, pp. 1-7, 2009.
Invitation to Pay Additional Fees mailed on Jul. 31, 2007, for PCT Application No. PCT/US2007/001624 filed on Jan. 19, 2007, five pages.
International Search Report and Written Opinion, International Application No. PCT/US2009/040629, mailed Aug. 6, 2009, 9 pages.
Restriction Requirement, U.S. Appl. No. 11/641,382, mailed Sep. 3, 2009, 6 pages.
International Search Report and Written Opinion, International Application No. PCT/US2009/051109, mailed Nov. 6, 2009, 13 pages.
NonFinal Office Action, U.S. Appl. No. 11/641,569, mailed Nov. 12, 2009, 9 pages.
Restriction Requirement, U.S. Appl. No. 11/656,323, mailed Nov. 13, 2009, 10 pages.
U.S. Appl. No. 13/374,960, filed Jan. 25, 2012, Pavlovskaia et al.
Amendment Under 37 C.F.R. 1.312, U.S. Appl. No. 13/374,960, filed May 7, 2013, 6 pages.
Final Office Action, U.S. Appl. No. 12/546,545, dated Dec. 20, 2012, 16 pages.
Final Office Action, U.S. Appl. No. 12/636,939, mailed Jan. 25, 2013, 9 pages.
Final Office Action, U.S. Appl. No. 12/563,809, mailed Mar. 7, 2013, 14 pages.
Non-Final Office Action, U.S. Appl. No. 11/641,569, dated Jan. 3, 2013, 12 pages.
Non-Final Office Action, U.S. Appl. No. 13/086,275, mailed Feb. 7, 2013, 36 pages.
Non-Final Office Action, U.S. Appl. No. 12/546,545, mailed Mar. 13, 2013, 10 pages.
Non-Final Office Action, U.S. Appl. No. 12/636,939, mailed Apr. 25, 2013, 16 pages.
Notice of Allowance, U.S. Appl. No. 11/641,382, mailed Feb. 6, 2013, 14 pages.
Notice of Allowance, U.S. Appl. No. 11/924,425, mailed Feb. 5, 2013, 16 pages.
Notice of Allowance, U.S. Appl. No. 12/111,924, dated Dec. 24, 2012, 10 pages.
Notice of Allowance, U.S. Appl. No. 29/394,882, mailed Feb. 4, 2013, 32 pages.

(56) References Cited

OTHER PUBLICATIONS

Notice of Allowance, U.S. Appl. No. 12/111,924, mailed Mar. 11, 2013, 14 pages.
Notice of Allowance, U.S. Appl. No. 13/374,960, mailed May 6, 2013, 20 pages.
Notice of Allowance, U.S. Appl. No. 13/573,662, mailed Mar. 19, 2013, 34 pages.
Response to Final Office Action, U.S. Appl. No. 12/546,545, filed Feb. 20, 2013, 13 pages.
Response to Final Office Action, U.S. Appl. No. 12/563,809, filed May 6, 2013, 15 pages.
Response to Final Office Action, U.S. Appl. No. 12/636,939, filed Apr. 8, 2013, 10 pages.
Response to Non-Final Office Action, U.S. Appl. No. 12/390,667, filed Feb. 26, 2013, 36 pages.
Response to Non-Final Office Action, U.S. Appl. No. 11/641,569, filed Apr. 3, 2013, 9 pages.
Response to Non-Final Office Action, U.S. Appl. No. 13/086,275, filed May 7, 2013, 11 pages.
Response to Restriction Requirement, U.S. Appl. No. 12/760,388, filed Apr. 5, 2013, 7 pages.
Response to Restriction, U.S. Appl. No. 13/573,662, filed Feb. 8, 2013, 8 pages.
Restriction Requirement, U.S. Appl. No. 13/573,662, mailed Jan. 17, 2013, 6 pages.
Restriction Requirement, U.S. Appl. No. 12/760,388, mailed Mar. 6, 2013, 7 pages.
U.S. Appl. No. 13/086,275, filed Apr. 13, 2011, Park et al.
U.S. Appl. No. 13/066,568, filed Apr. 18, 2011, Pavlovskaia et al.
U.S. Appl. No. 29/394,882, filed Jun. 22, 2011, Ilwhan Park.
Amendment and Response to Ex Parte Quayle Action, U.S. Appl. No. 29/296,687, dated Mar. 24, 2011, 17 pages.
Amendment and Response to Non-Final Office Action, U.S. Appl. No. 11/959,344, dated Jul. 15, 2011, 13 pages.
European Search Report, 10192631.9-2310, dated Mar. 17, 2011, 5 pages.
Ex Parte Quayle Action, U.S. Appl. No. 29/296,687, mailed Jan. 24, 2011, 11 pages.
International Search Report and Written Opinion, PCT/US2011/032342, dated Jul. 1, 2011, 8 pages.
Nonfinal Office Action, U.S. Appl. No. 11/959,344, dated Feb. 15, 2011, 29 pages.
Non-Final Office Action, U.S. Appl. No. 11/641,569, dated Aug. 3, 2011, 14 pages.
Notice of Allowance, U.S. Appl. No. 29,296,687, mailed Mar. 31, 2011, 18 pages.
Response to Restriction Requirement, U.S. Appl. No. 11/959,344, filed Nov. 24, 2010, 13 pages.
Response to Restriction Requirement, U.S. Appl. No. 12/390,667, dated Jul. 27, 2011, 8 pages.
Restriction Requirement, U.S. Appl. No. 12/390,667, dated Jul. 14, 2011, 9 pages.
Restriction Requirement, U.S. Appl. No. 12/391,008, dated Aug. 18, 2011, 6 pages.
U.S. Appl. No. 13/488,505, filed Jun. 5, 2012, Ilwhan Park et al.
Advisory Action and Interview Summary, U.S. Appl. No. 12/390,667, mailed Apr. 27, 2012, 23 pages.
Amendment Under 37 C.F.R. 1.312, U.S. Appl. No. 12/386,105, filed Oct. 1, 2012, 6 pages.
Appeal Brief, U.S. Appl. No. 12/390,667, filed Jul. 12, 2012, 32 pages.
Final Office Action, U.S. Appl. No. 11/641,382, mailed Jul. 25, 2012, 12 pages.
Final Office Action, U.S. Appl. No. 11/924,425, mailed Jul. 6, 2012, 14 pages.
Final Office Action, U.S. Appl. No. 11/946,002, mailed May 9, 2012, 24 pages.
Final Office Action, U.S. Appl. No. 12/391,008, mailed May 17, 2012, 28 pages.
Non-Final Office Action, U.S. Appl. No. 11/641,382, mailed Mar. 29, 2012, 24 pages.
Non-Final Office Action, U.S. Appl. No. 12/111,924, mailed Jun. 29, 2012, 35 pages.
Non-Final Office Action, U.S. Appl. No. 12/390,667, mailed Sep. 26, 2012, 21 pages.
Non-Final Office Action, U.S. Appl. No. 12/546,545, mailed Jul. 19, 2012, 28 pages.
Non-Final Office Action, U.S. Appl. No. 12/563,809, mailed Sep. 21, 2012, 32 pages.
Non-Final Office Action, U.S. Appl. No. 12/636,939, mailed Jul. 20, 2012, 25 pages.
Non-Final Office Action, U.S. Appl. No. 13/374,960, mailed Aug. 1, 2012, 6 pages.
Notice of Allowance, U.S. Appl. No. 11/924,425, mailed Sep. 25, 2012, 18 pages.
Notice of Allowance, U.S. Appl. No. 12/386,105, mailed Jul. 5, 2012, 11 pages.
RCE/Amendment, U.S. Appl. No. 11/946,002, filed Sep. 6, 2012, 38 pages.
Response to Final Office Action, U.S. Appl. No. 11/641,569, filed Jun. 28, 2012, 10 pages.
Response to Final Office Action, U.S. Appl. No. 11/641,382, filed Sep. 24, 2012, 11 pages.
Response to Final Office Action, U.S. Appl. No. 11/924,425, filed Sep. 5, 2012, 9 pages.
Response to Non-Final Office Action, U.S. Appl. No. 11/924,425, filed Apr. 25, 2012, 8 pages.
Response to Non-Final Office Action, U.S. Appl. No. 12/386,105, filed Jun. 8, 2012, 13 pages.
Response to Non-Final Office Action, U.S. Appl. No. 11/641,382, filed Jun. 27, 2012, 12 pages.
Response to Non-Final Office Action, U.S. Appl. No. 12/111,924, filed Sep. 28, 2012, 10 pages.
Response to Restriction Requirement, U.S. Appl. No. 12/111,924, filed Apr. 16, 2012, 8 pages.
Response to Restriction Requirement, U.S. Appl. No. 12/636,939, filed Apr. 19, 2012, 6 pages.
Response to Restriction, U.S. Appl. No. 12/563,809, filed Aug. 6, 2012, 10 pages.
Response to Restriction, U.S. Appl. No. 12/505,056, filed Apr. 11, 2012, 9 pages.
Response to Restriction, U.S. Appl. No. 12/546,545, filed Jun. 4, 2012, 7 pages.
Restriction Requirement, U.S. Appl. No. 12/546,545, mailed May 3, 2012, 8 pages.
Restriction Requirement, U.S. Appl. No. 12/563,809, mailed Jul. 6, 2012, 6 pages.
Restriction Requirement, U.S. Appl. No. 12/636,939, mailed Apr. 13, 2012, 6 pages.
Amendment and Response to Non-Final Office Action, U.S. Appl. No. 11/641,382, dated Apr. 20, 2010, 23 pages.
Amendment and Response to Office Action, U.S. Appl. No. 11/641,569, dated Feb. 5, 2010, 20 pages.
Amendment and Response to Restriction Requirement, U.S. Application No. 11/641,569, dated May 27, 2009, 12 pages.
Amendment and Response to Restriction Requirement, U.S. Appl. No. 11/641,382, dated Oct. 5, 2009, 10 pages.
Amendment and Response to Restriction/Election Requirement, U.S. Appl. No. 11/656,323, filed Dec. 8, 2009, 6 pages.
Amendment and Response to Office Action, U.S. Appl. No. 11/656,323, filed Jun. 25, 2010, 7 pages.
Final Office Action and PTO-892, U.S. Appl. No. 11/641,382, mailed Aug. 5, 2010, 13 pages.
Final Office Action, U.S. Appl. No. 11/641,569, mailed May 10, 2010, 9 pages.
Final Office Action and PTO-892, U.S. Appl. No. 11/656,323, mailed Sep. 3, 2010, 11 pages.
International Preliminary Report on Patentability, PCT/US2009/034983, dated Sep. 10, 2010, 13 pages.
International Search Report and Written Opinion, International Application No. PCT/US2009/058946, mailed Jan. 28, 2010, 14 pages.

(56) References Cited

OTHER PUBLICATIONS

International Search Report and Written Opinion, International Application No. PCT/US2009/068055, mailed Mar. 11, 2010, 10 pages.
Non-Final Office Action and PTO-892, U.S. Appl. No. 11/641,382, mailed Jan. 20, 2010, 12 pages.
Non-Final Office Action and PTO-892, U.S. Appl. No. 11/656,323, mailed Mar. 30, 2010, 10 pages.
Notice of Non-Compliant Amendment, U.S. Appl. No. 11/641,569, mailed Aug. 7, 2009, 3 pages.
Preliminary Amendment, U.S. Appl. No. 11/641,569, dated Aug. 14, 2008, 13 pages.
RCE/Amendment, U.S. Appl. No. 11/641,569, filed Aug. 9, 2010.
RCE/Amendment, U.S. Appl. No. 11/642,382, filed Oct. 26, 2010, 14 pages.
RCE/Amendment, U.S. Appl. No. 11/656,323, filed Nov. 19, 2010, 12 pages.
Response to Notice of Non-Complaint Amendment, U.S. Appl. No. 11/641,569, dated Aug. 19, 2009, 11 pages.
Response to Restriction Requirement U.S. Appl. No. 29/296,687, filed Oct. 7, 2010, 3 pages.
Restriction Requirement, U.S. Appl. No. 29/296,687, mailed Sep. 21, 2010, 7 pages.
Restriction Requirement, U.S. Appl. No. 11/959,344, dated Oct. 29, 2010, 6 pages.
AKCA, "Matching of 3D Surfaces and Their Intensities," ISPRS Journal of Photogrammetry & Remote Sensing, 62(2007), 112-121.
Arima et al., "Femoral Rotational Alignment, Based on the Anteroposterior Axis, in Total Knee Arthroplasty in a Valgus Knee. A Technical Note," Journal Bone Joint Surg Am. 1995;77(9):1331-4.
Bargar et al., "Robotic Systems in Surgery," Orthopedic and Spine Surgery, Surgical Technology International II, 1993, 419-423.
Besl et al., "A Method for Registration of 3-D Shapes," IEEE Transactions on Pattern Analysis and Machine Intelligence (PAMI), 14(2):239-256, Feb. 1992.
Blaha et al., "Using the Transepicondylar Axis to Define the Sagittal Morphology of the Distal Part of the Femur," J Bone Joint Surg Am. 2002;84-A Suppl 2:48-55.
Bullough et al., "The Geometry of Diarthrodial Joints, Its Physiologic Maintenance and the Possible significance of Age-Related Changes in Geometry-to-Load distribution and the Development of Osteoarthritis," Clin Orthop Rel Res 1981, 156:61-6.
Burgkart et al., "Magnetic Resonance Imaging-Based Assessment of Cartilage Loss in Severe Osteoarthritis: Accuracy, Precision, and Diagnostic Value," Arthritis Rheum 2001, 44:2072-7.
Canny, "A computational Approach to Edge Detection," IEEE Transactions on Pattern Analysis and Machine Intelligence, PAMI 8(6), pp. 679-698 (1986).
Churchill et al., "The Transepicondylar Axis Approximates the Optimal Flexion Axis of the Knee," Clin Orthop Relat Res. 1998(356):111-8.
Cicuttini et al., "Gender Differences in Knee Cartilage Volume as Measured by Magnetic Resonance Imaging," Osteoarthritis Cartilage 1999, 7:265-71.
Cicuttini et al., "Longitudinal Study of the Relationship Between Knee angle and Tibiofemoral cartilage Volume in Subjects with Knee Osteoarthritis," Rheumatology (Oxford) 2004, 43:321-4.
Eckhoff et al., "Difference Between the Epicondylar and Cylindrical Axis of the Knee," Clin Orthop Relat Res. 2007;461:238-44.
Eisenhart-Rothe et al., "Femorotibial and Patellar Cartilage Loss in Patients Prior to Total Knee arthroplasty, Heterogeneity, and Correlation with alignment of the Knee," Ann Rheum Dis., Jun. 2005 (BMJ Publishing Group Ltd & European League Against Rheumatism).
Eisenhart-Rothe et al., "The Role of Knee alignment in Disease Progression and Functional Decline in Knee Osteoarthritis," JAMA 2001, 286:188-95.
Elias et al., "A Correlative Study of the Geometry and anatomy of the Distal Femur," Clinical Orthopaedics and Related Research 1990(260):98-103.
Favorito et al., "total Knee Arthroplasty in the Valgus Knee," Journal Am Acad Orthop surg. 2002;10(1):16-24.
Freeman et al., "The Movement of the Knee Studied by Magnetic Resonance Imaging," Clinical Orthopaedics and Related Research 2003(410):35-43.
Freeman et al., "The Movement of the Normal Tibio-Femoral Joint," Journal Biomech. 2005;38(2):197-208.
Graichen et al., "Quantitative Assessment of Cartilage Status in Osteoarthritis by Quantitative Magnetic Resonance Imaging: Technical Validation for Use in analysis of Cartilage Volume and Further Morphologic Parameters," Arthritis Rheum 2004, 50:811-16.
Gruen et al., "Least Squares 3D Surface and Curve Matching," ISPRS Journal of Photogrammetry & Remote Sensing, 59(2005), 151-174.
Hollister et al., "The Axes of Rotation of the Knee," Clinical Orthopaedics and Related Research 1993(290):259-68.
Howell et al., "Longitudinal Shapes of the Tibia and Femur are Unrelated and Variable," Clinical Orthopaedics and Related Research (2010) 468: 1142-1148.
Howell et al., "Results of an Initial Experience with Custom-Fit Positioning Total Knee Arthroplasty in a Series of 48 Patients," Orthopedics, 2008;31(9):857-63.
Howell et al., "In Vivo Adduction and Reverse Axial Rotation (External) of the Tibial Component can be Minimized During Standing and Kneeling," Orthopedics, In Press.
Iwaki et al., "Tibiofemoral Movement 1: The Shapes and Relative Movements of the Femur and Tibia in the Unloaded Cadaver Knee," Journal Bone Joint Surg Br. 2000;82(8):1189-95.
Jacobs et al., "Hip Resurfacing Through an Anterolateral Approach," J. Bone Joint Surg Am. 2008:90 Suppl 3:38-44.
Johnson, "Joint Remodeling as the Basis for Osteoarthritis," Journal Am Vet Med Assoc. 1962, 141:1233-41.
Kass et al., "Active Contour Models," International Journal of Computer Vision, pp. 321-331 (1988).
Kellgren et al., "Radiological Assessment of Osteoarthrosis," Ann Rheum Dis 1957, 10:494-501.
Kessler et al, "Sagittal Curvature of Total Knee Replacements Predicts in vivo Kinematics," Clin Biomech (Bristol, Avon) 2007; 22(1):52-8.
Kienzel III et al., "Total Knee Replacement," IEEE May/Jun. 1995.
Kienzel III et al., "An Integrated CAD-Robotics System for Total Knee Replacement Surgery", IEEE International Conference, pp. 889-894, vol. 1, May 1993.
Krackow et al., "Flexion-Extension Joint Gap Changes After Lateral Structure Release for Valgus Deformity Correction in Total Knee Arthroplasty: A Cadaveric Study," Journal Arthroplasty, 1999;14(8):994-1004.
Krackow et al., "Primary Total Knee Arthroplasty in Patients with Fixed Valgus Deformity," Clin Orthop Relat Res. 1991(273):9-18.
Krackow, "Approaches to Planning lower Extremity alignment for Total Knee arthroplasty and Osteotomy About the Knee," adv Orthop surg 7:69, 1983.
Lea et al., "Registration and immobilization in robot-assisted surgery", Journal of Image Guided Surgery, pp. 1-10, 1995.
Manner et al., "Knee Deformity in Congenital Longitudinal Deficiencies of the Lower Extremity," Clin Orthop Relat Res. 2006;448:185-92.
Matsuda et al., "Anatomical Analysis of the Femoral Condyle in Normal and Osteoarthritic Knees," Journal Orthopaedic Res. 2004;22(1):104-9.
Matsuda et al., "Femoral Condyle Geometry in the Normal and Varus Knee," Clinical Orthop Relat Res. 1998(349):183-8.
Messmer et al., "Volumetric Model Determination of the Tibia Based on 2d Radiographs Using a 2d/3d Database", Dept. of Surgery, Trauma Unit, University Hospital, Basel, Switzerland, *Computer Aided Surgery* 6:183-194 (2001).
Mihalko et al., The Variability of Intramedullary Alignment of the Femoral Component During Total Knee Arthroplasty, Journal Arthroplasty. 2005;20(1):25-8.

(56) References Cited

OTHER PUBLICATIONS

Morvan et al., IVECS, Interactively Correcting .STL Files in a Virtual Environment, Clemson University, Clemson, SC, Proc. Conf. Virtual Design, Aug. 1996.
Naoki Kusumoto, Taiji et al., "Application of Virtual Reality Force Feedback Haptic Device for Oral Implant Surgery", Graduate School of Dentistry Course for Integrated Oral Science and Stomatology, Jun. 16, 2005.
Panjabi et al., "Errors in Kinematic Parameters of a Planar Joint: Guidelines for Optimal Experimental Design," Journal Biomech. 1982;15(7):537-44.
Perillo-Marcone et al., "Effect of Varus/Valgus Malalignment on Bone Strains in the Proximal Tibia After TKR: An Explicit Finite element Study," Journal Biomechanical Engineering 2007, vol. 129, 1:1-11.
Peterfy et al., "Quantification of articular Cartilage in the Knee with Pulsed Saturation Transfer Subtraction and Fact-Suppressed MR Imaging: Optimization and Validation," Radiology 1994, 192:485-91.
Pinskerova et al., "The Shapes and Relative Movements of the Femur and Tibia at the Knee," Orthopaedics 2000;29 Suppl 1:S3-5.
Rosset et al., "General Consumer Communication Tools for Improved Image Management and Communication in Medicine," Journal Digital Imaging, 2005;18(4):270-9.
Shakespeare D., "Conventional Instruments in Total Knee Replacement: What Should We Do With Them?" Knee. 2006;13(1):1-6.
Shepstone et al., "The shape of the Distal Femur: A Palaeopathological Comparison of Eburnated and Non-Eburnated Femora," Ann. Rheum Dis. 1999, 58:72-8.
Siston et al., "The Variability of Femoral Rotational Alignment in Total Knee Arthroplasty," Journal Bone Joint Surg Am. 2005;87(10):2276-80.
Siston et al., "Averaging Different Alignment Axes Improves Femoral Rotational Alignment in Computer-Navigated Total Knee Arthroplasty," Journal Bone Joint Surg Am. 2008;90(10):2098-104.
Soudan et al., "Methods, Difficulties and Inaccuracies in the Study of Human Joint Kinematics and Pathokinematics by the Instant axis Concept. Example: The Knee Joint," Journal Biomech. 1979;12(1):27-33.
Spencer et al., "Initial Experience with Custom-Fit Total Knee Replacement: Intra-operative Events and Long-Leg Coronal alignment," International Orthopaedics (SICOT), 2009:In Press.
Stulberg et al., "Computer- and Robot-Assisted Orthopaedic Surgery", Computer-Integrated Surgery Technology and Clinical Applications, edited by Taylor et al., Massachusetts Institute of Technology, Chapter 27, pp. 373-378, 1996.
Teeny et al., "Primary Total Knee Arthroplasty in Patients with Severe Varus Deformity. A Comparative Study," Clin Orthop Relat Res. 1991(273):19-31.
Wright Medical Technology, Inc., "Prophecy Pre-Operative Naviation Guides Surgical Technique," 2009.
U.S. Appl. No. 13/573,662, filed Oct. 2, 2012, Pavlovskaia et al.
Howell et al., "In Vivo Adduction and Reverse Axial Rotation (External) of the Tibial Component can be Minimized During Standing and Kneeling," Orthopedics|ORTHOSupersite.com vol. 32 No. 5, 319-326 (May 2009).
Appeal Brief, U.S. Appl. No. 12/391,008, filed Oct. 16, 2012, 24 pages.
Examiner's Answer in appeal, U.S. Appl. No. 12/391,008, mailed Dec. 13, 2012, 27 pages.
Notice of Allowance, U.S. Appl. No. 11/641,382, mailed Oct. 9, 2012, 9 pages.
Notice of Allowance, U.S. Appl. No. 13/374,960, mailed Nov. 2, 2012, 24 pages.
Response to Non-Final Office Action, U.S. Appl. No. 12/636,939, filed Oct. 10, 2012, 8 pages.
Response to Non-Final Office Action, U.S. Appl. No. 12/546,545, filed Oct. 19, 2012, 15 pages.
Response to Non-Final Office Action, U.S. Appl. No. 12/563,809, filed Dec. 13, 2012, 15 pages.
Final Office Action, U.S. Appl. No. 11/959,344, mailed Oct. 27, 2011, 12 pages.
Final Office Action, U.S. Appl. No. 12/390,667, mailed Jan. 13, 2012, 27 pages.
Final Office Action, U.S. Appl. No. 11/641,569, mailed Mar. 1, 2012, 12 pages.
Non-Final Office Action, U.S. Appl. No. 11/924,425, mailed Jan. 25, 2012, 35 pages.
Non-Final Office Action, U.S. Appl. No. 12/390,667, dated Aug. 24, 2011, 49 pages.
Non-Final Office Action, U.S. Appl. No. 11/946,002, dated Nov. 25, 2011, 44 pages.
Non-Final Office Action, U.S. Appl. No. 12/386,105, dated Feb. 9, 2012, 30 pages.
Non-Final Office Action, U.S. Appl. No. 12/391,008, mailed Oct. 31, 2011, 44 pages.
Notice of Allowance, U.S. Appl. No. 13/066,568, mailed Oct. 26, 2011, 28 pages.
Notice of Allowance, U.S. Appl. No. 11/959,344, mailed Mar. 5, 2012, 13 pages.
Office Action (Restriction Requirement), U.S. Appl. No. 12/563,809, dated Feb. 2, 2012, 7 pages.
Response to Final Office Action, U.S. Appl. No. 11/959,344, filed Dec. 27, 2011, 16 pages.
Response to final Office Action, U.S. Appl. No. 12/390,667, filed Mar. 12, 2012, 19 pages.
Response to Non-Final Office Action, U.S. Appl. No. 12/390,667, filed Nov. 18, 2011, 16 pages.
Response to Non-Final Office Action, U.S. Appl. No. 11/641,569, filed Dec. 2, 2011, 7 pages.
Response to Non-Final Office Action, U.S. Appl. No. 12/391,008, filed Feb. 24, 2012, 18 pages.
Response to Non-Final Office Action, U.S. Appl. No. 11/946,002, filed Mar. 8, 2012, 16 pages.
Response to Restriction Requirement, U.S. Appl. No. 12/391,008, filed Aug. 29, 2011, 9 pages.
Response to Restriction Requirement, U.S. Appl. No. 12/386,105, filed Dec. 21, 2011, 9 pages.
Response to Restriction Requirement, U.S. Appl. No. 12/563,809, filed Feb. 24, 2012, 10 pages.
Response to Restriction, U.S. Appl. No. 11/924,425, filed Nov. 8, 2011, 5 pages.
Response to Restriction, U.S. Appl. No. 11/946,002, filed Sep. 23, 2011, 7 pages.
Restriction Requirement, U.S. Appl. No. 11/924,425, dated Oct. 13, 2011, 6 pages.
Restriction Requirement, U.S. Appl. No. 11/946,002, dated Sep. 1, 2011, 8 pages.
Restriction Requirement, U.S. Appl. No. 12/111,924, mailed Mar. 19, 2012, 8 pages.
Restriction Requirement, U.S. Appl. No. 12/386,105, dated Oct. 24, 2011, 7 pages.
Restriction Requirement, U.S. Appl. No. 12/505,506, mailed Mar. 14, 2012, 8 pages.
U.S. Appl. No. 13/723,904, filed Dec. 21, 2012, Park.
U.S. Appl. No. 13/730,467, filed Dec. 28, 2012, Park et al.
U.S. Appl. No. 13/730,585, filed Dec. 28, 2012, Park et al.
U.S. Appl. No. 13/730,608, filed Dec. 28, 2012, Park et al.
U.S. Appl. No. 13/731,697, filed Dec. 31, 2012, Pavlovskaia et al.
U.S. Appl. No. 13/731,850, filed Dec. 31, 2012, Park.
U.S. Appl. No. 13/749,095, filed Jan. 24, 2013, Song.
U.S. Appl. No. 13/960,498, filed Aug. 6, 2013, Song.
U.S. Appl. No. 14/084,255, filed Nov. 19, 2013, Park et al.
U.S. Appl. No. 14/086,849, filed Nov. 21, 2013, Park et al.
U.S. Appl. No. 14/086,878, filed Nov. 21, 2013, Park et al.
Audette et al. "An algorithmic overview of surface registration techniques for medical imaging." Medical Image Analysis, vol. 4, No. 3, Sep. 1, 2000, pp. 201-217.
European Search Report, EP09739422.5, dated Mar. 28, 2013, 9 pages.
Final Office Action, U.S. Appl. No. 11/641,569, dated Nov. 29, 2013, 20 pages.

(56) References Cited

OTHER PUBLICATIONS

Final Office Action, U.S. Appl. No. 12/390,667, dated Oct. 25, 2013, 17 pages.
Final Office Action, U.S. Appl. No. 12/505,056, dated Dec. 30, 2013, 48 pages.
Final Office Action, U.S. Appl. No. 12/546,545, dated Oct. 7, 2013, 24 pages.
Final Office Action, U.S. Appl. No. 13/723,904, dated Dec. 24, 2013, 10 pages.
Final Office Action, U.S. Appl. No. 13/730,585, dated Dec. 27, 2013, 8 pages.
Ibáñez et al., The ITK Software Guide, Second Edition, Updated for ITK version 2.4, Nov. 21, 2005, pp. 114, 396-411, and 426.
Japanese Office Action, JP Application No. 2011-507530, dated Dec. 17, 2013, 8 pages.
Non-Final Office Action, U.S. Appl. No. 11/641,569, mailed Jul. 12, 2013, 21 pages.
Non-Final Office Action, U.S. Appl. No. 11/656,323, dated Oct. 22, 2013, 36 pages.
Non-Final Office Action, U.S. Appl. No. 11/946,002, dated Oct. 2, 2013, 39 pages.
Non-Final Office Action, U.S. Appl. No. 11/946,002, dated Feb. 6, 2014, 46 pages.
Non-Final Office Action, U.S. Appl. No. 12/390,667, mailed May 8, 2013, 20 pages.
Non-Final Office Action, U.S. Appl. No. 12/505,056, mailed Jun. 28, 2013, 7 pages.
Non-Final Office Action, U.S. Appl. No. 12/760,388, mailed Jun. 20, 2013, 54 pages.
Non-Final Office Action, U.S. Appl. No. 13/723,904, mailed Aug. 9, 2013, 6 pages.
Non-Final Office Action, U.S. Appl. No. 13/730,467, dated Jan. 15, 2014, 8 pages.
Non-Final Office Action, U.S. Appl. No. 13/730,585, mailed Jun. 11, 2013, 10 pages.
Non-Final Office Action, U.S. Appl. No. 13/730,608, dated Oct. 7, 2013, 10 pages.
Notice of Allowance, Design U.S. Appl. No. 29/394,882, mailed May 24, 2013, 16 pages.
Notice of Allowance, U.S. Appl. No. 11/641,569, dated Feb. 5, 2014, 11 pages.
Notice of Allowance, U.S. Appl. No. 12/390,667, dated Jan. 17, 2014, 9 pages.
Notice of Allowance, U.S. Appl. No. 12/546,545, dated Dec. 26, 2013, 9 pages.
Notice of Allowance, U.S. Appl. No. 12/563,809, mailed May 28, 2013, 11 pages.
Notice of Allowance, U.S. Appl. No. 12/636,939, dated Oct. 7, 2013, 28 pages.
Notice of Allowance, U.S. Appl. No. 12/760,388, dated Jan. 22, 2014, 13 pages.
Notice of Allowance, U.S. Appl. No. 13/086,275, mailed Aug. 27, 2013, 31 pages.
Preliminary Amendment, U.S. Appl. No. 13/731,697, filed May 10, 2013, 6 pages.
Response to Final Office Action, U.S. Appl. No. 11/641,569, dated Jan. 29, 2014, 10 pages.
Response to Final Office Action, U.S. Appl. No. 12/390,667, dated Dec. 23, 2013, 5 pages.
Response to Final Office Action, U.S. Appl. No. 12/546,545, dated Dec. 9, 2013, 8 pages.
Response to Non-Final Office Action, U.S. Appl. No. 12/546,545, filed Jul. 15, 2013, 14 pages.
Response to Non-Final Office Action, U.S. Appl. No. 12/636,939, filed Jul. 16, 2013, 15 pages.
Response to Non-Final Office Action, U.S. Appl. No. 12/390,667, filed Aug. 7, 2013, 22 pages.
Response to Non-Final Office Action, U.S. Appl. No. 12/760,388, filed Sep. 12, 2013, 15 pages.
Response to Non-Final Office Action, U.S. Appl. No. 12/505,056, filed Oct. 9, 2013, 17 pages.
Response to Non-Final Office Action, U.S. Appl. No. 13/730,585, filed Oct. 9, 2013, 15 pages.
Response to Non-Final Office Action, U.S. Appl. No. 11/641,569, filed Oct. 11, 2013, 12 pages.
Response to Non-Final Office Action, U.S. Appl. No. 13/723,904, filed Nov. 6, 2013, 8 pages.
Response to Non-Final Office Action, U.S. Appl. No. 11/946,002, filed Dec. 6, 2013, 18 pages.
Response to Non-Final Office Action, U.S. Appl. No. 13/730,608, dated Jan. 7, 2014, 16 pages.
Response to Non-Final Office Action, U.S. Appl. No. 11/656,323, dated Jan. 17, 2014, 10 pages.
Siemens MAGNETOM Sonata 1.5T Technical Specifications, pp. 1-4, accessed online Jan. 28, 2014.
Xie et al. "Segmentation by surface-to-image registration." proceedings of SPIE, vol. 6144, Mar. 2, 2006, pp. 614405-1-614405-7.
Extended European Search Report, European Appl. No. 08863202.1, dated May 16, 2014.
Notice of Allowance, U.S. Appl. No. 13/730,467, dated May 5, 2014.
Notice of Allowance, U.S. Appl. No. 13/731,850, dated Jun. 6, 2014.
Response to Non-Final Office Action, U.S. Appl. No. 11/946,002, dated Jul. 7, 2014.
Response to Restriction, U.S. Appl. No. 13/488,505, dated May 5, 2014, 7 pages.

* cited by examiner

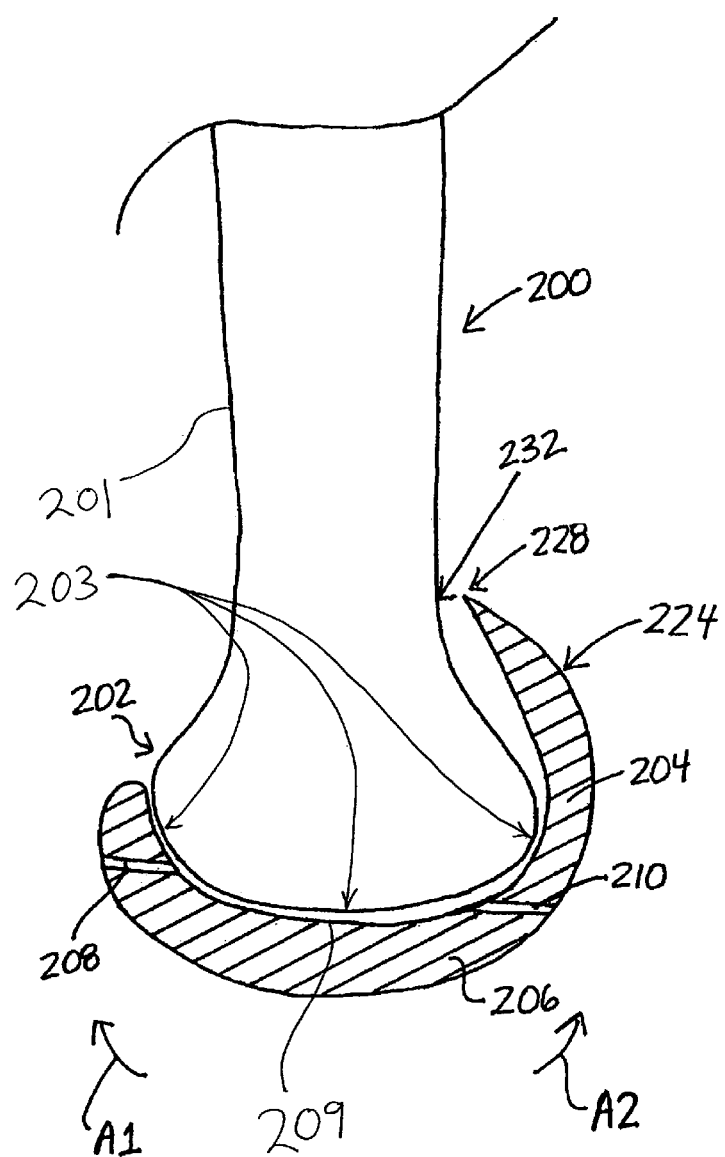

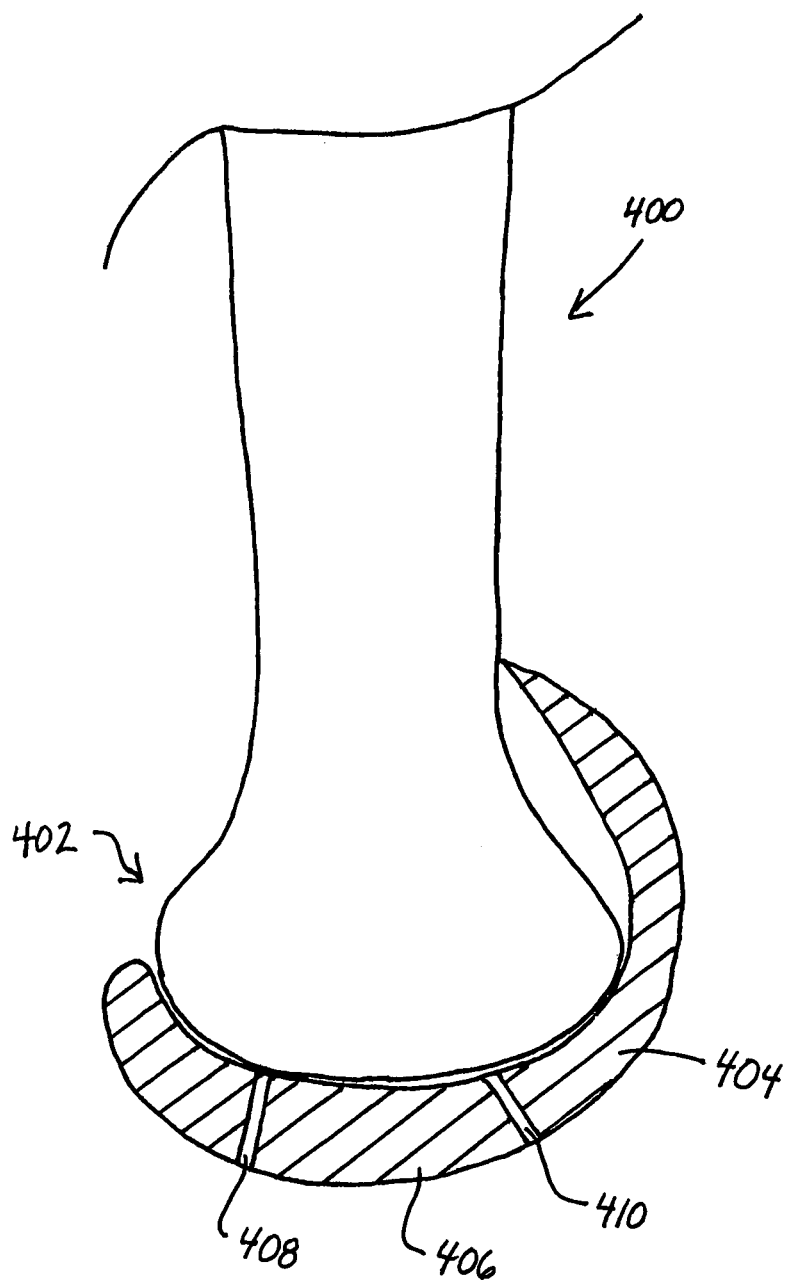

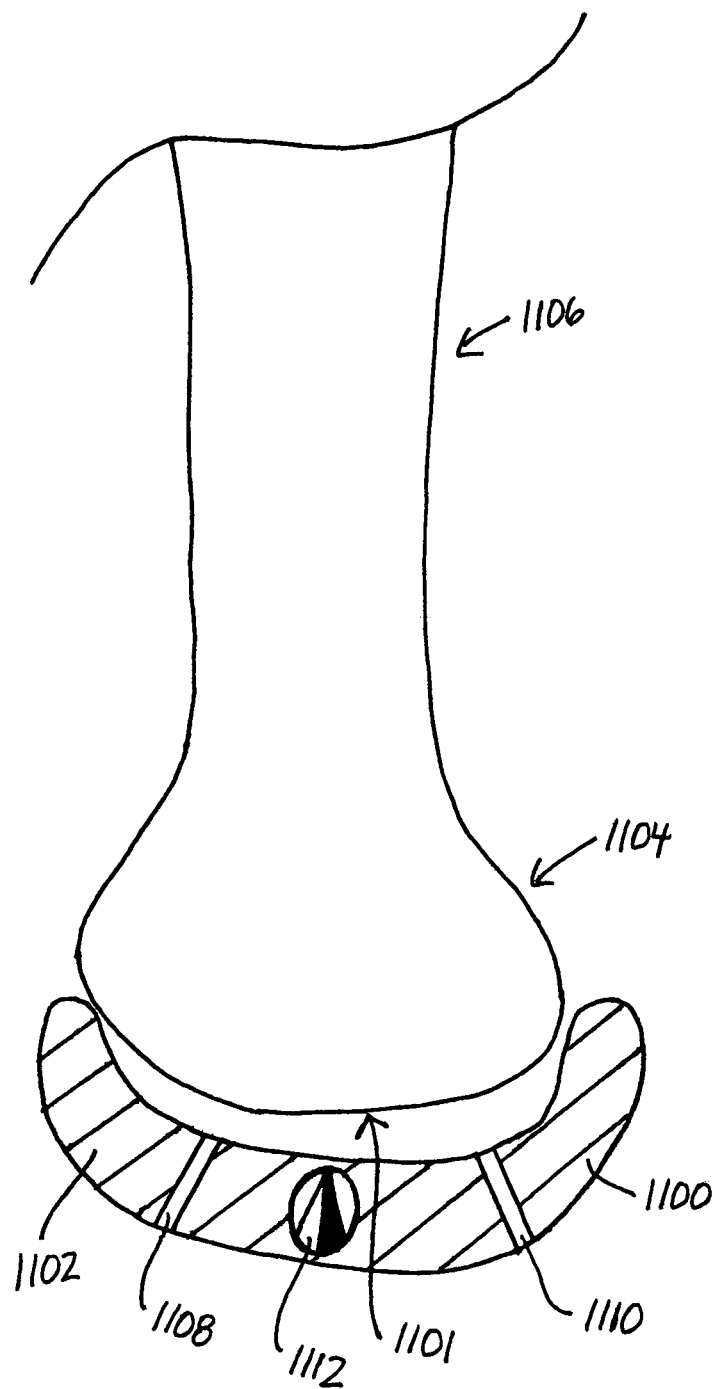

ARTHROPLASTY DEVICES AND RELATED METHODS

CROSS-REFERENCE TO RELATED APPLICATIONS

This application claims the benefit of priority, under 35 U.S.C. §119(e), to U.S. Pat. Appl. Ser. No. 60/773,491, filed on Feb. 15, 2006, which is hereby incorporated by reference in its entirety.

TECHNICAL FIELD

The methods and devices described herein relate generally to the field of implants, as well as jigs that may be used to position and align implants at a target site. More specifically, the methods and devices described herein relate to the field of selecting an arthroplasty jig that corresponds to a specific target site, and accurately positioning and aligning the arthroplasty jig at the target site.

BACKGROUND

Over time and through repeated use, bones and joints can become damaged or worn. For example, repetitive strain on bones and joints (e.g., through athletic activity), traumatic events, and certain diseases (e.g., arthritis) can cause cartilage in joint areas to wear down. As a result, fluid can accumulate in these joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

As mentioned above, during some arthroplasty procedures, an implant may be implanted into the damaged region. The implant may provide support and structure to the damaged region, and may help to restore the damaged region, thereby enhancing its functionality. Prior to implantation of the implant in the damaged region, the damaged region can be prepared to receive the implant. For example, in a knee arthroplasty procedure, one or more of the bones in the knee area, such as the femur and/or tibia, may be treated (e.g., cut, drilled, reamed, and/or resurfaced) to provide one or more surfaces that can align with the implant and thereby accommodate the implant.

Prior to treating any regions of a bone, it is important to correctly determine the location at which the treatment will take place. In some methods, an arthroplasty jig may be used to accurately position an instrument, such as a cutting, drilling, reaming, or resurfacing instrument, at a target site. The instrument can, in turn, be used to prepare the target site for an implant prior to delivery of the implant to the target site. The arthroplasty jig may, for example, include one or more apertures and/or slots that are configured to accept the instrument.

In order for an arthroplasty jig to accurately position an instrument at a target site, however, the arthroplasty jig itself should be accurately positioned and aligned at the target site. Accordingly, it would be desirable to provide methods and devices that allow for identification and selection of the correct arthroplasty jig for use at a particular target site, as well as methods and devices that allow for the precise positioning and alignment of an arthroplasty jig at a target site.

BRIEF SUMMARY

Described here are methods and devices that may be used to help identify a suitable arthroplasty jig for use at a target site, as well as methods and devices that may be used to enhance the positioning and alignment of an arthroplasty jig at a target site. The methods and devices described here include certain features that may enhance the customization of an arthroplasty procedure, and may thereby result in reduced procedure time and recovery time, as well as a reduced likelihood of complications.

Some of the arthroplasty jigs described here comprise a jig body that is configured to align with a surface of a bone, and a positioning component that is configured to provide at least one of a visible, audible, or tactile indication when the jig body has aligned with the surface of the bone. Similarly, some of the methods described here comprise providing an arthroplasty jig comprising a jig body and a positioning component, and aligning the jig body with a surface of a bone so that the positioning component provides at least one of a visible, audible, or tactile indication that such alignment has been achieved. The methods may further comprise cutting, drilling, reaming, and/or resurfacing the bone. The presence of the positioning component as part of the arthroplasty jig may increase the likelihood that this cutting, drilling, reaming, and/or resurfacing occurs in the right location.

Certain of the arthroplasty jigs described here comprise a jig body that is marked with identifying information, and that is configured to align with a surface of a bone. Similarly, certain of the arthroplasty jig blanks described here (which are used to form arthroplasty jigs) are marked with identifying information. Some of the methods described here comprise providing an arthroplasty jig blank, or an arthroplasty jig comprising a jig body that is configured to align with a surface of a bone, and marking the arthroplasty jig blank or the jig body with identifying information. The markings on an arthroplasty jig blank may decrease the likelihood of the wrong arthroplasty jig blank being selected to form a particular arthroplasty jig. An arthroplasty jig that is formed from an arthroplasty jig blank may retain some or all of the markings that originally were on the arthroplasty jig blank, and thus may be readily identifiable. The markings on a marked arthroplasty jig may be used, for example, to assist in positioning and aligning the arthroplasty jig at a target site, and/or to readily identify the arthroplasty jig prior to or during an arthroplasty procedure.

Arthroplasty jigs, arthroplasty jig blanks, and related methods may include just one of the features described herein, or more than one of the features described herein. For example, in some variations, an arthroplasty jig may include both a positioning component and one or more markings that provide identifying information about the arthroplasty jig.

The positioning component may be attached to the jig body, or may be integrally formed with the jig body. In some variations, the positioning component may comprise a rod. In such variations, the jig body may comprise an aperture, and the positioning component may at least partially extend through the aperture. In certain variations, the positioning component may comprise a projection extending from the jig body. In some variations, the positioning component may be hook-shaped.

In certain variations in which the jig body is marked with identifying information, the identifying information may be engraved into the jig body, printed onto the jig body, and/or provided on a label that is affixed to the jig body. Examples of engraving methods include carving, cutting, and etching (e.g., laser etching). The identifying information may include, for example, patient data, doctor information, information regarding the size and/or materials of the jig body, company logos, barcodes, etc.

The arthroplasty jig may be configured for use in at least one of cutting, drilling, reaming, or resurfacing a bone during an arthroplasty procedure. For example, the jig body may comprise at least one slot or aperture that is configured to accept an instrument, such as a cutting instrument (e.g., a reciprocating saw blade). The jig body may be configured so that the cutting instrument can be used in conjunction with the arthroplasty jig to remove a portion of a bone to provide a substantially planar surface on the bone. The substantially planar surface, in turn, may be configured to align with a surface of an implant device. Examples of bones with which the arthroplasty jigs and methods may be used include femurs and tibias.

BRIEF DESCRIPTION OF THE DRAWINGS

FIG. 2C is an illustration of the portion of the femur of FIG. 2A, when the arthroplasty jig of FIG. 2A is not aligned with the portion of the femur.

FIG. 4 is an illustration of a portion of a femur of a subject, and an arthroplasty jig aligned with the portion of the femur.

FIG. 11B is an illustration of the portion of the femur of FIG. 11A, when the arthroplasty jig of FIG. 11A is not aligned with the portion of the femur.

DETAILED DESCRIPTION

Described here are arthroplasty jigs, and methods of making and using arthroplasty jigs, having features that may provide for enhanced alignment and positioning of the arthroplasty jigs at a target site. This enhanced arthroplasty jig alignment and positioning may, in turn, result in enhanced implant alignment and positioning at the target site. As the implant alignment and positioning of an implant are improved, the result may be a decreased likelihood of follow-up surgery (e.g., to adjust the alignment of the implant), and/or an increase in the useful life of the implant. Additional results may include reduced procedure time and fewer complications during and/or after surgery. It should be understood from the outset that while knee arthroplasty jigs are described in detail here, one or more of the features or methods described here may be employed with other types of arthroplasty jigs, such as arthroplasty jigs that are suited for use in the hip, shoulder, elbow, etc.

Figure 1:
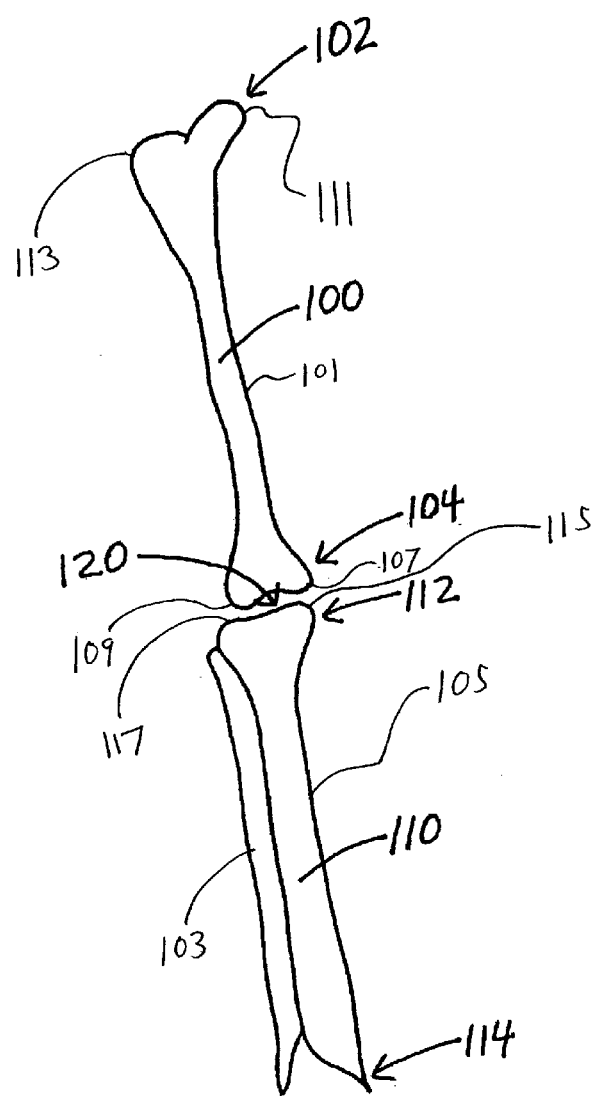
FIG. 1 is an illustration of leg bones of a subject.

Turning now to the figures, FIG. 1 is an illustration of the anterior sides of the leg bones of a human subject. As shown in FIG. 1, the leg bones include a femur (100) having a proximal end (102) and a distal end (104), a tibia (110) having a proximal end (112) and a distal end (114), and a fibula (103) extending generally parallel to the tibia (110). The femur (100) includes a shaft (101) that extends between the proximal end (102) and the distal end (104), and the tibia (110) includes a shaft (105) that extends between the proximal end (112) and the distal end (114). The femur distal end (104) includes a knee joint region that articulates with a corresponding knee joint region of the tibia proximal end (112) and includes a medial condyle (107) and a lateral condyle (109). The femur proximal end (102) combines with the pelvis to form the hip joint and includes a head (111) and a greater trochanter (113). The tibia proximal end (112) includes a knee joint region that articulates with the corresponding knee joint region of the femur distal end (104) and includes a medial plateau (115) and a lateral plateau (117). A joint (120) is formed between the femoral distal end (104)

and the tibial proximal end (112), and may, as a result of damage or wear, require repair or restoration using, for example, an arthroplasty procedure.

As discussed above, in some variations of an arthroplasty procedure, one or more arthroplasty jigs may be used to help prepare a damaged bone region for an implant. The arthroplasty jigs may be used, for example, to aid in the correct placement of certain instruments, such as cutting, drilling, reaming, and resurfacing instruments. As an example, some arthroplasty procedures may include using an arthroplasty jig to accurately position a reciprocating saw blade. The reciprocating saw blade may be used, for example, to cut the damaged bone region to provide one or more planar surfaces. The planar surfaces may assist in the alignment and positioning of an implant at a target site in the damaged bone region. Arthroplasty jigs may also be used, for example, to position one or more pins that secure an implant to a target site in the damaged bone region.

Figure 2A:
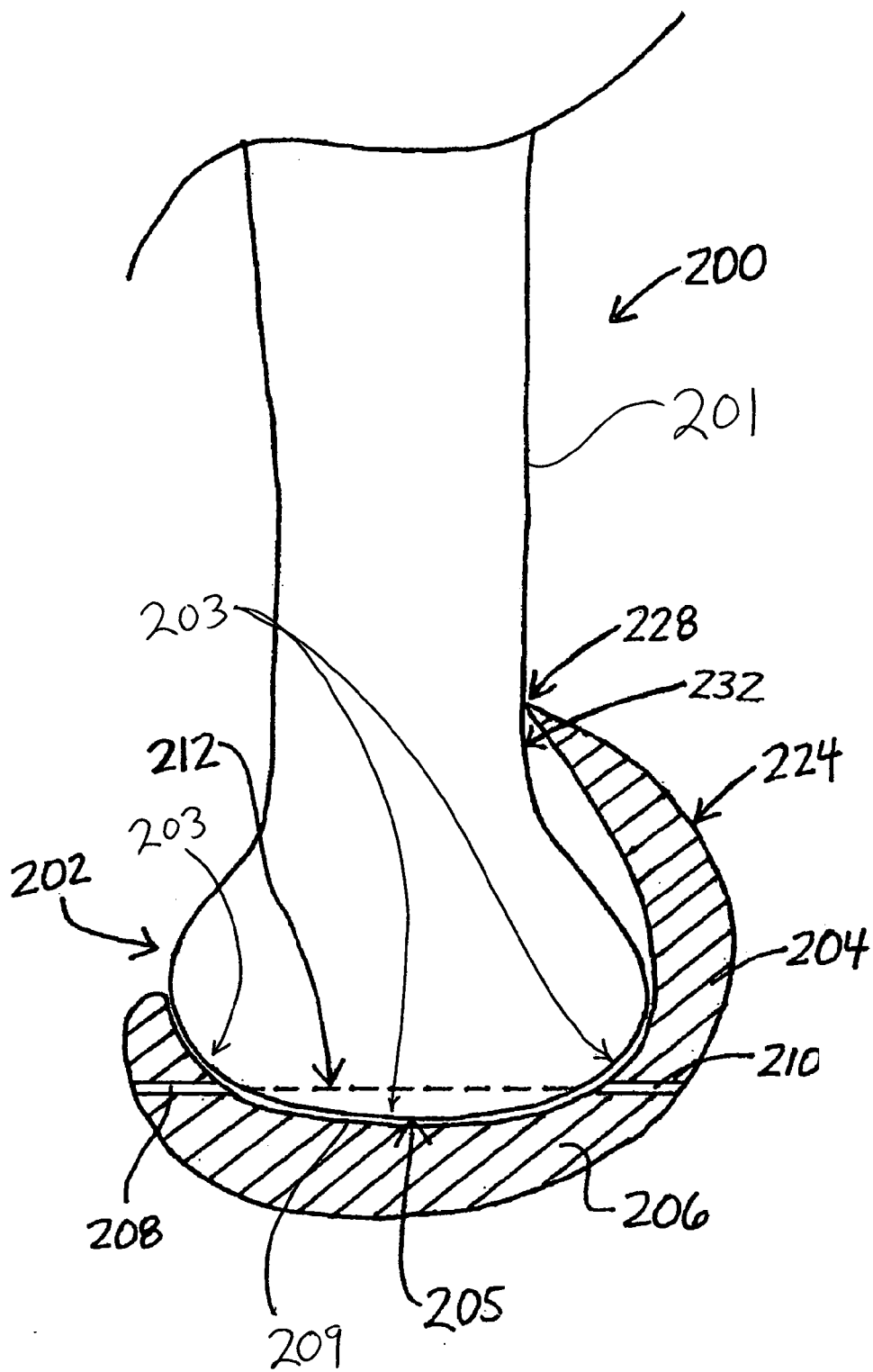
FIG. 2A is an illustration of a portion of a femur of a subject, and an arthroplasty jig aligned with the portion of the femur.
Figure 2B:
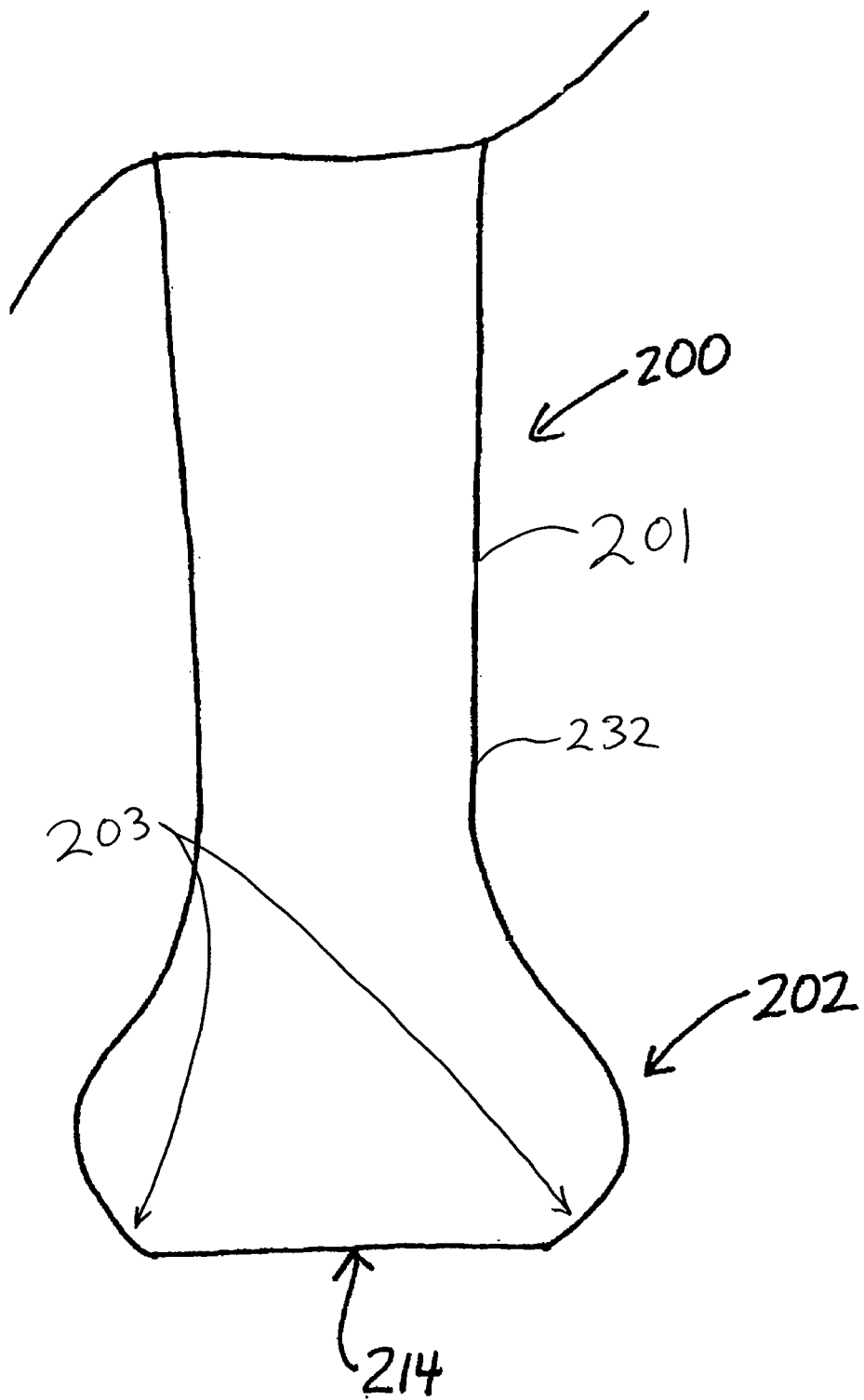
FIG. 2B is an illustration of the portion of the femur of FIG. 2A, after the portion has been cut using a cutting instrument.

A femoral arthroplasty jig is shown in FIG. 2A. As shown in FIG. 2A, a femur (200) has a femoral distal end (202) distally extending from the femoral shaft (201) and including a condyle region (203). An arthroplasty jig (204) includes a surface (209) that is aligned with a surface (205) of condyle region (203), and has a jig body (206) including two slots (208) and (210). Slots (208) and (210) can be used, for example, to position a cutting instrument (e.g., a reciprocating saw blade). The cutting instrument, in turn, can be used to form a cut (212) that removes a portion of distal end (202) of femur (200). The result, as shown in FIG. 2B, is a planar surface (214) along distal end (202) of femur (200). Planar surface (214) may, for example, align with a corresponding planar surface of an implant that is implanted into a damaged region of the knee that is at least partially defined by femur (200).

Referring back to FIG. 2A, arthroplasty jig (204) includes a positioning component (as shown, a projection (224)) that is integrally formed with jig body (206). Projection (224) has a pointed end (228). FIG. 2A shows arthroplasty jig (204) when it has been properly aligned with surface (205) of distal end (202) of femur (200), as indicated by projection (224) contacting a surface (232) of femur (200), for example, the femoral shaft surface (232). As a physician is positioning arthroplasty jig (204) on femur (200), the contact between pointed end (228) and femoral shaft surface (232) can provide the physician with a tactile indication that the arthroplasty jig has been properly positioned and aligned on femur (200). In other words, the physician may sense the contact between the pointed end and the surface of the femoral shaft. This contact may feel different to the physician, relative to the contact between other portions of arthroplasty jig (204) and femur (200). For example, at the other contact points, the arthroplasty jig may actually be contacting cartilage, whereas pointed end (228) contacts bone when arthroplasty jig (204) is properly positioned and aligned. Contact between an arthroplasty jig and cartilage typically feels different from contact between an arthroplasty jig and bone. Upon sensing the contact between pointed end (228) and shaft surface (232) of femur (200), the physician knows that the desired alignment has been achieved, and that the arthroplasty jig can stop being adjusted.

Figure 2D:
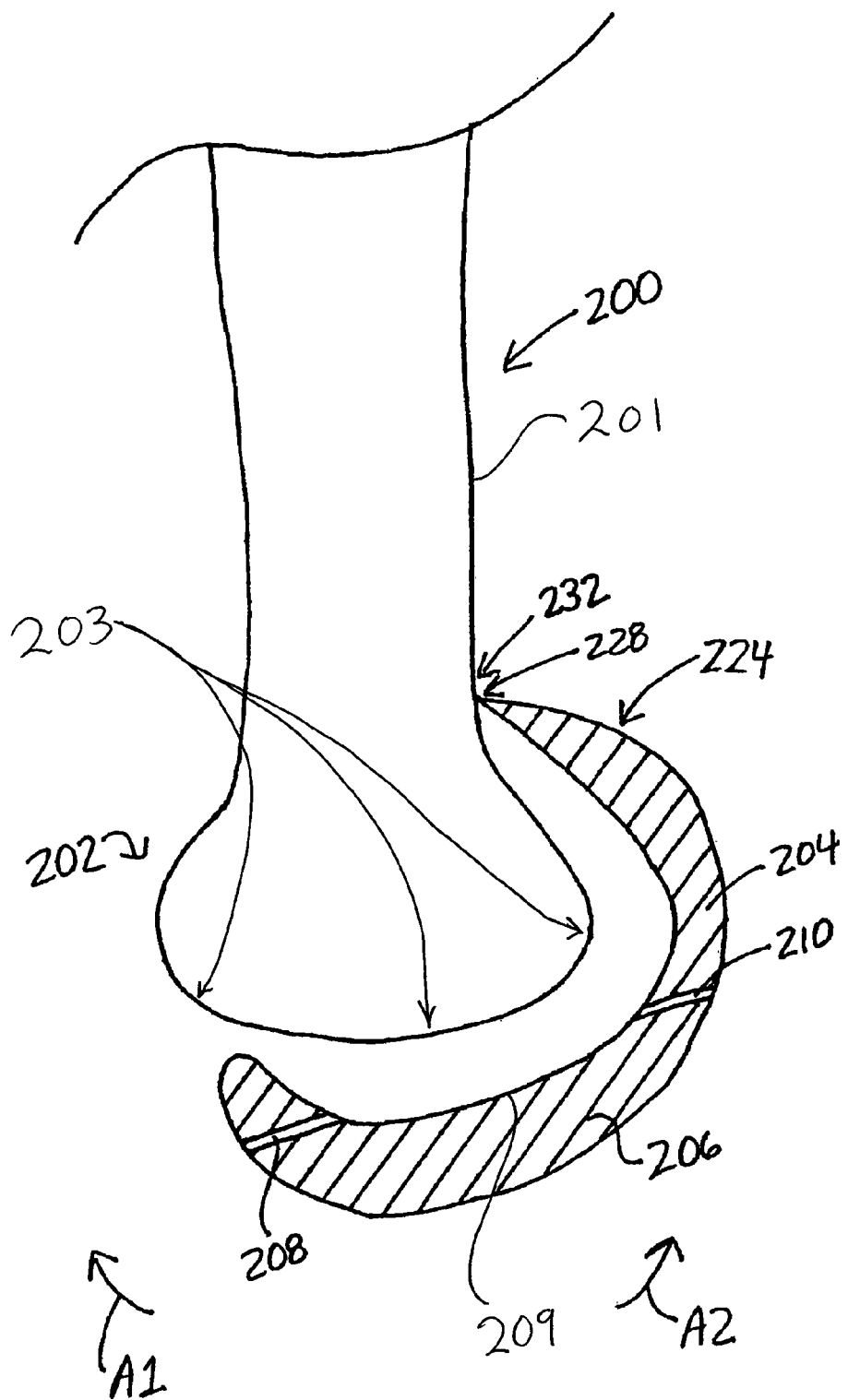
FIG. 2D is an illustration of the portion of the femur of FIG. 2A, when the arthroplasty jig of FIG. 2A is not aligned with the portion of the femur.

FIGS. 2C and 2D show arthroplasty jig (204) when it has not been properly positioned and aligned on femur (200). In FIG. 2C, arthroplasty jig (204) is positioned too far in the direction of arrow (A1), and not far enough in the direction of arrow (A2). Accordingly, and as shown in FIG. 2C, pointed end (228) of projection (224) does not contact shaft surface (232) of femur (200). FIG. 2D, on the other hand, shows arthroplasty jig (204) when it has been moved too far in the direction of arrow (A2). This may occur, for example, if the physician does not stop adjusting the arthroplasty jig after pointed end (228) has contacted shaft surface (232), and instead continues to move the arthroplasty jig in the direction of arrow (A2). The result is that jig body (206) pivots about the point of contact between pointed end (228) and shaft surface (232). This pivoting sensation notifies the physician that the position of the arthroplasty jig should be adjusted back in the direction of arrow (A1), rather than arrow (A2).

Figure 3A:
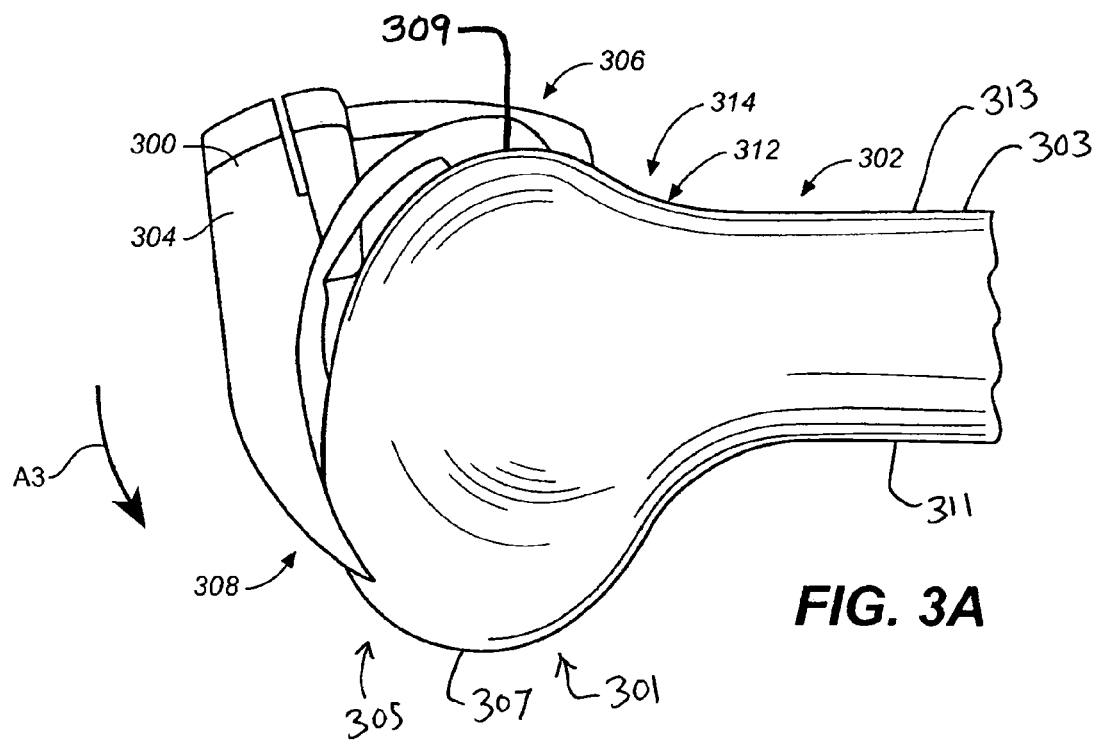
FIG. 3A is an illustration of a portion of a femur of a subject, and an arthroplasty jig being positioned on the portion of the femur.
Figure 3B:
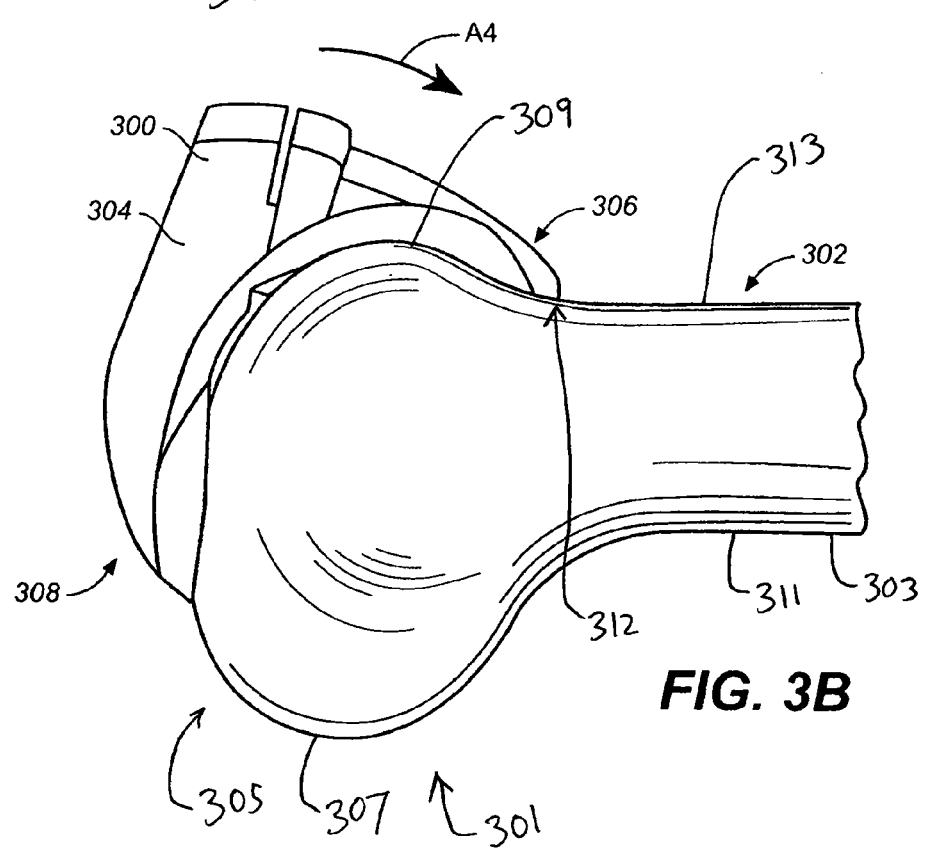
FIG. 3B is an illustration of the portion of the femur of FIG. 3A, and the arthroplasty jig of FIG. 3A being positioned on the portion of the femur.

FIGS. 3A and 3B show another variation of an arthroplasty jig (300) on a femoral distal end (301) extending from a femoral shaft (303). The femoral distal end (301) includes a condyle region (305) with a posterior side (307) and an anterior side (309), and the femoral shaft (303) includes a posterior side (311) and anterior side (313). In FIG. 3A, arthroplasty jig (300) is being positioned on a distal portion of a femur (302). Arthroplasty jig (300) includes a jig body (304) and projections (306) and (308) that extend from opposite ends of jig body (304) and that are integrally formed with jig body (304). When arthroplasty jig (300) is properly positioned on femur (302), projection (306) contacts an inflection point (312) on femur (302). For example, projection (306) contacts the anterior femoral shaft surface (312). However, and as FIG. 3A shows, if the physician adjusts arthroplasty jig (300) too far in the direction of arrow (A3), then projection (308) will become a pivoting point, and projection (306) will slide over a surface (314) of femur (302), away from inflection point (312). This misalignment of arthroplasty jig (300) may be visible to the physician. Furthermore, and referring now to FIG. 3B, if the physician tries to adjust arthroplasty jig (300) too far in the direction of arrow (A4), then projection (306) similarly becomes a pivoting point that indicates that arthroplasty jig (300) has not been properly positioned on femur (302).

While the slots in some of the above arthroplasty jigs (such as slots (208) and (210) of arthroplasty jig (204)) have been described as being useful for positioning a cutting instrument, some variations of arthroplasty jigs may include one or more slots and/or apertures that are configured for other purposes. As an example, FIG. 4 shows a femur (400) having a distal end (402), as well as an arthroplasty jig (404) that is aligned with distal end (402). Arthroplasty jig (404) includes a jig body (406) having two apertures (408) and (410). Apertures (408) and (410) may be used, for example, to assist in the placement of one or more pins that help to secure an implant to femur (400).

While arthroplasty jigs having one or two slots or apertures have been shown, arthroplasty jigs can have any number of slots, apertures, grooves, and/or ridges. The number and type of features on an arthroplasty jig may be selected, for example, based on the proposed modifications to the target site. Arthroplasty jigs can also be configured for use in forming more than one planar surface in a damaged bone region. For example, an arthroplasty jig may be used to form two or three planar surfaces in a damaged bone region. The multiple planar surfaces may correspond to multiple planar surfaces in an implant that is to be inserted into the damaged bone region. Moreover, the slots, apertures, grooves, and/or ridges may be used for other purposes besides the aforementioned cutting, drilling, reaming, resurfacing, and pin positioning. For example, grooves and/or ridges on an arthroplasty jig may provide the arthroplasty jig with a surface morphology that helps the arthroplasty jig to be accurately positioned at a target site.

Figure 5A:
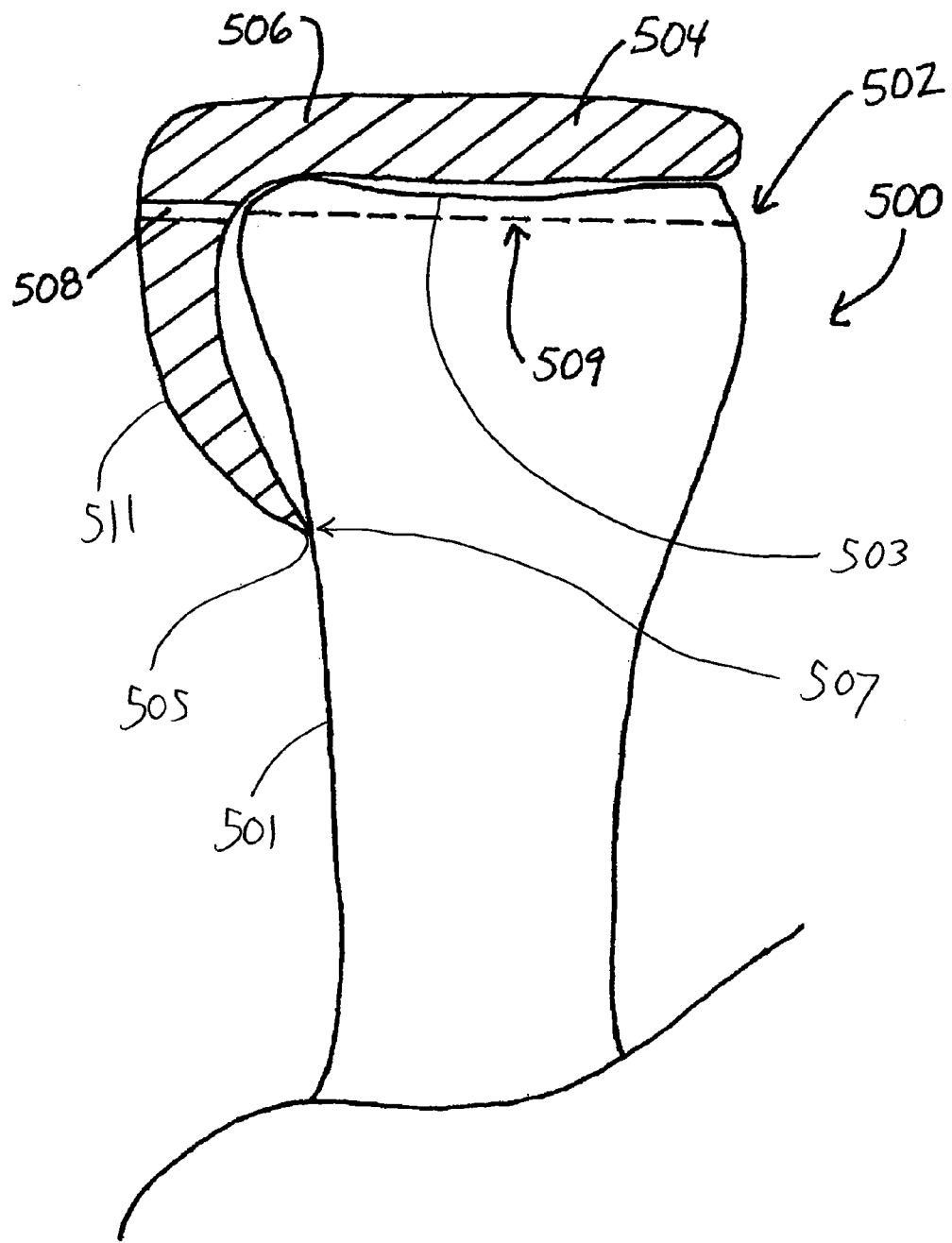
FIG. 5A is an illustration of a portion of a tibia of a subject, and an arthroplasty jig aligned with the portion of the tibia.
Figure 5B:
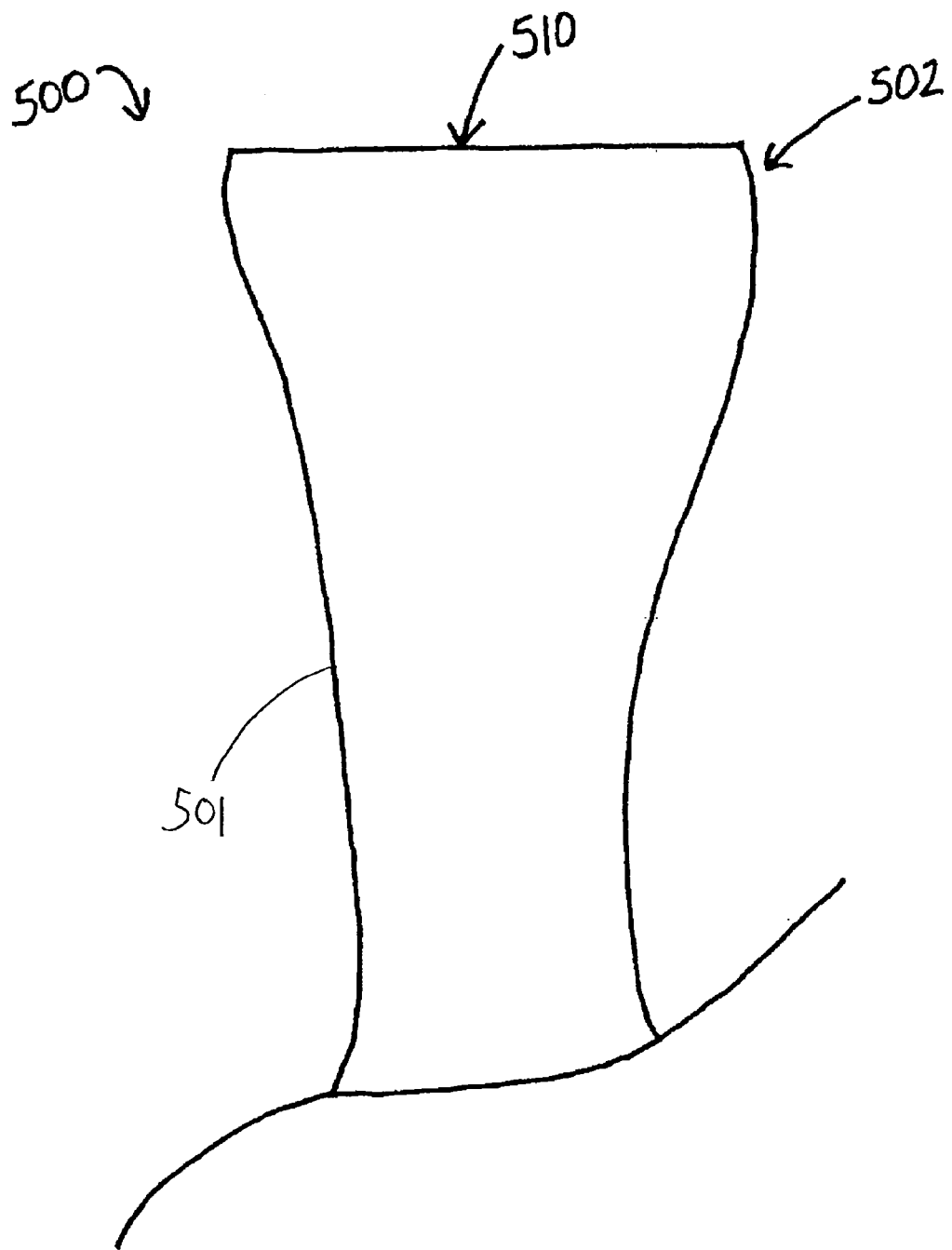
FIG. 5B is an illustration of the portion of the tibia of FIG. 5A, after the portion has been cut using a cutting instrument.

Arthroplasty jigs may be used in many other regions of the body besides a femur. For example, FIG. 5A shows a tibial arthroplasty jig. As shown in FIG. 5A, a tibia (500) has a proximal end (502) proximally extending from the tibia shaft (501) and including a plateau region (503). An arthroplasty jig (504) is aligned with proximal end (502), and has a body (506) including a slot (508). Slot (508) can be used to position a cutting instrument (e.g., a reciprocating saw blade) that, in turn, can be used to form a cut (509) in proximal end (502) of tibia (500). The result, as shown in FIG. 5B, is a planar surface (510) along proximal end (502) of tibia (500). Planar surface (510) may, for example, align with a corresponding planar surface of an implant that is implanted into a damaged region of the knee that is at least partially defined by tibia (500).

While the arthroplasty jigs shown above include positioning components in the form of projections (224), (511) having pointed ends (228), (505) that contact femoral and tibia bone surfaces, e.g., femoral shaft surfaces (232) and tibia shaft surfaces (507), arthroplasty jigs may include other types of positioning components. As an example, an arthroplasty jig may include a positioning component in the form of a projection having a rounded end. Positioning components may be integrally formed with, or attached to, the jig body of an arthroplasty jig. Examples of methods that may be used to attach a positioning component to a jig body include welding and bonding (e.g., adhesive-bonding). While arthroplasty jigs with one positioning component have been described, some arthroplasty jigs may include multiple positioning components, such as two, three, four, five, or ten positioning components. The positioning components may be the same type of positioning component, or different types of positioning components. As an example, an arthroplasty jig may include both a positioning component in the form of a projection having a pointed end, and a positioning component in the form of a projection having a rounded end.

Figure 6A:
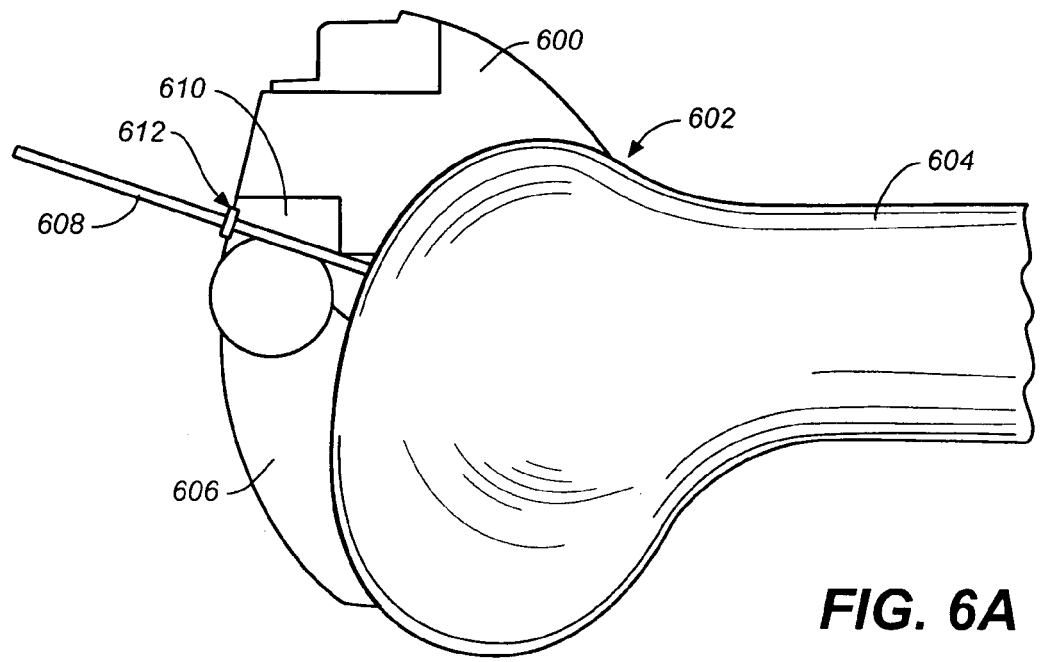
FIG. 6A is an illustration of a portion of a femur of a subject, and an arthroplasty jig aligned with the portion of the femur.
Figure 6B:
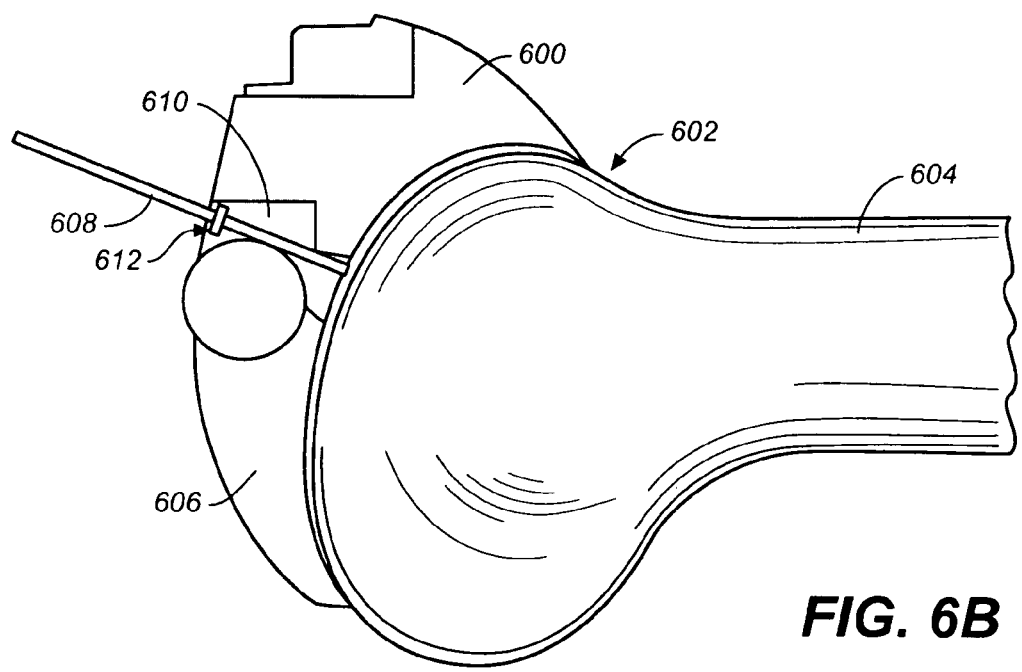
FIG. 6B is an illustration of the portion of the femur of FIG. 6A, when the arthroplasty jig of FIG. 6A is not aligned with the portion of the femur.

In some variations, an arthroplasty jig may include one or more positioning components that are neither integrally formed with, nor permanently attached to, its jig body. As an example, FIG. 6A shows an arthroplasty jig (600) that is aligned with a distal end (602) of a femur (604). Arthroplasty jig (600) includes a jig body (606) and a positioning component (as shown, a rod (608)) extending through an aperture (610) in jig body (606). A collar (612) surrounds rod (608), and may be used by a physician to determine whether arthroplasty jig (600) has been correctly positioned and aligned on distal end (602) of femur (604). More specifically, when the physician is positioning arthroplasty jig (600) on femur (604), the physician may advance rod (608) through aperture (610), until rod (608) contacts a surface of femur (604). At this point, the physician can check the position of collar (612), which will indicate whether arthroplasty jig (600) is in the correct position. If collar (612) is just outside of aperture (610), as shown in FIG. 6A, then arthroplasty jig (600) is correctly aligned. By contrast, if collar (612) is either not visible or not just outside of aperture (610), then the physician knows that arthroplasty jig (600) is not yet correctly aligned. For example, FIG. 6B shows arthroplasty jig (600) when it is not correctly aligned with femur (604). Collar (612) is disposed within aperture (610), thereby indicating that proper alignment has not yet been achieved.

In certain variations, collar (612) may be a different color from rod (608) and/or jig body (606). For example, rod (608) may be black and jig body (606) may be white, while collar (612) is green. This difference in color may enhance the visibility of collar (612), which may, in turn, enhance the ability of a physician to readily determine whether arthroplasty jig (600) is correctly aligned with femur (604).

Moreover, while FIGS. 6A and 6B show a rod and a collar, other types of positioning components may be used. As an example, a rod may include measurement markings (e.g., millimeter markings) that allow a physician to determine how deeply the rod has advanced into an aperture in a jig body. In certain variations, the rod may also include a collar or one or more other types of markers. Furthermore, in some variations, an arthroplasty jig may include one or more pins, springs, and/or wires (e.g., as an alternative to a rod or in addition to a rod). In certain variations, a positioning component may not be disposed within an aperture of a jig body. For example, an arthroplasty jig may include a jig body and a positioning component, such as a rod, which is movably attached to an outer surface of the jig body.

Arthroplasty jigs may have other positioning components that can provide a physician with a tactile indication of correct alignment. Additional examples of arthroplasty jigs that provide a physician with a tactile indication of correct alignment are described with reference to FIGS. 7A-9.

Figure 7A:
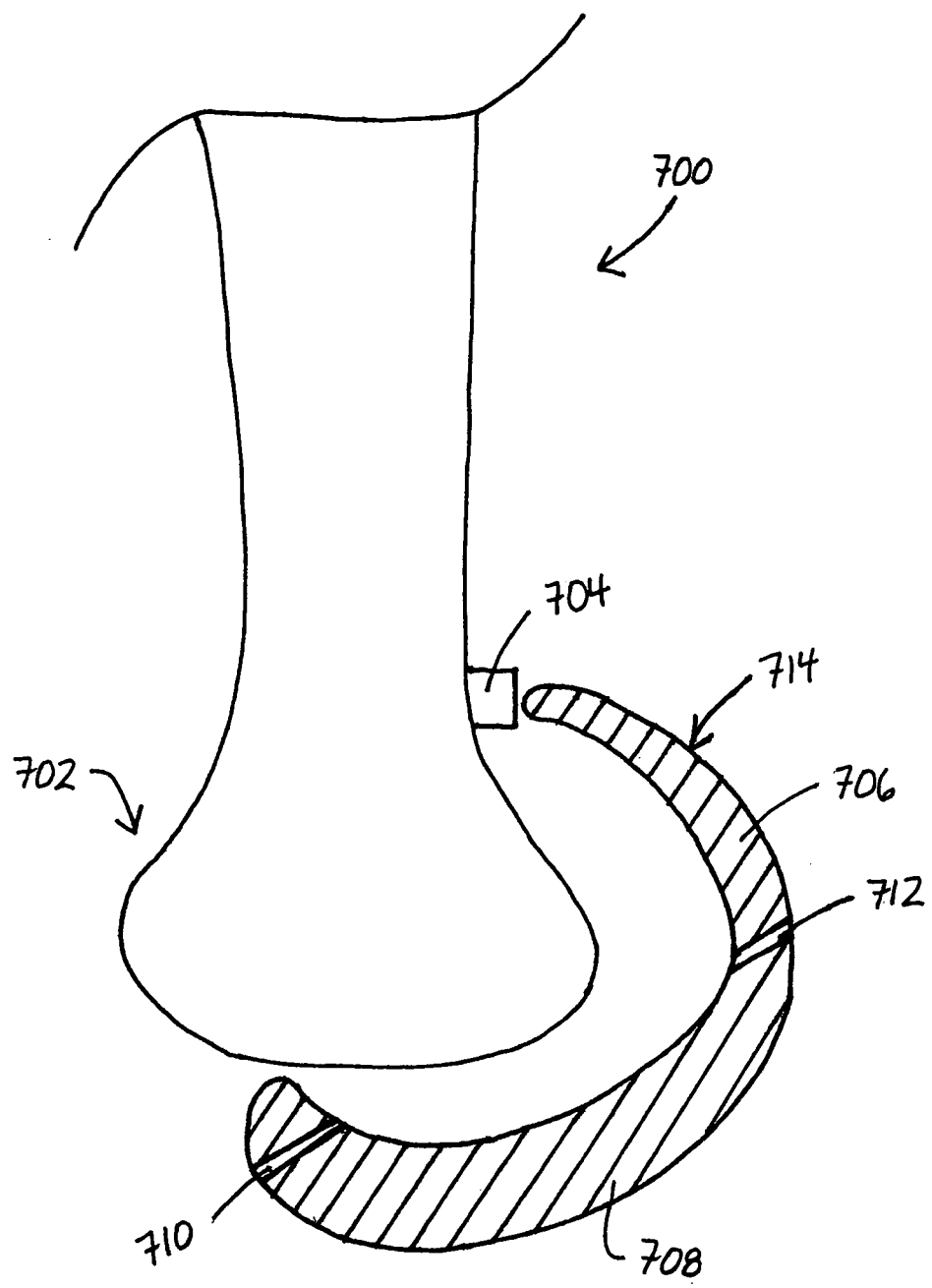
FIG. 7A is an illustration of an arthroplasty jig as the arthroplasty jig is being positioned on a portion of a femur of a subject.
Figure 7B:
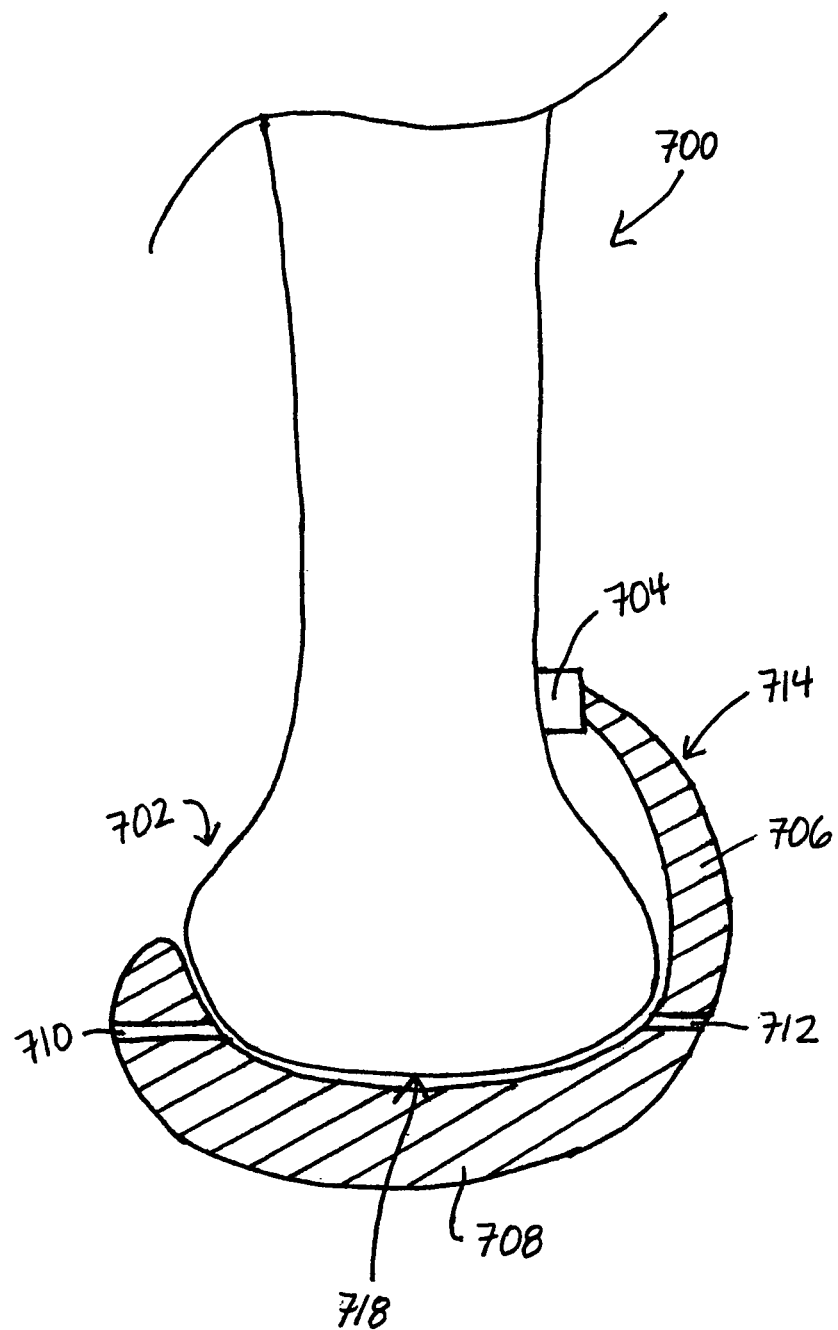
FIG. 7B is an illustration of the arthroplasty jig of FIG. 7A, after it has been aligned with the portion of the femur of FIG. 7A.

FIG. 7A shows a femur (700) having a distal end (702) and a lock (704) secured to distal end (702). In some variations, lock (704) may be temporarily secured to distal end (702) using, for example, an adhesive. FIG. 7A also shows an arthroplasty jig (706) including a jig body (708) having two slots (710) and (712), and a projection (714) extending from jig body (708). In FIG. 7A, arthroplasty jig (706) is being positioned so that projection (714) faces lock (704). FIG. 7B shows arthroplasty jig (706) when projection (714) has been locked or snapped into lock (704), and jig body (708) has been aligned with a surface (718) of femur (700). The sensation of projection (714) locking or snapping into lock (704) may provide a physician with a tactile indication that arthroplasty jig (706) has been correctly positioned for alignment with surface (718) of femur (700). Furthermore, there may be a sound associated with projection (714) locking or snapping into lock (704), which can provide a physician with an audible indication that arthroplasty jig (706) has been correctly positioned for alignment with surface (718) of femur (700). Additionally, by locking or snapping projection (714) into lock (704), a physician can temporarily secure jig body (708) to femur (700), so that jig body (708) may exhibit little or no movement during the arthroplasty procedure.

Figure 8A:
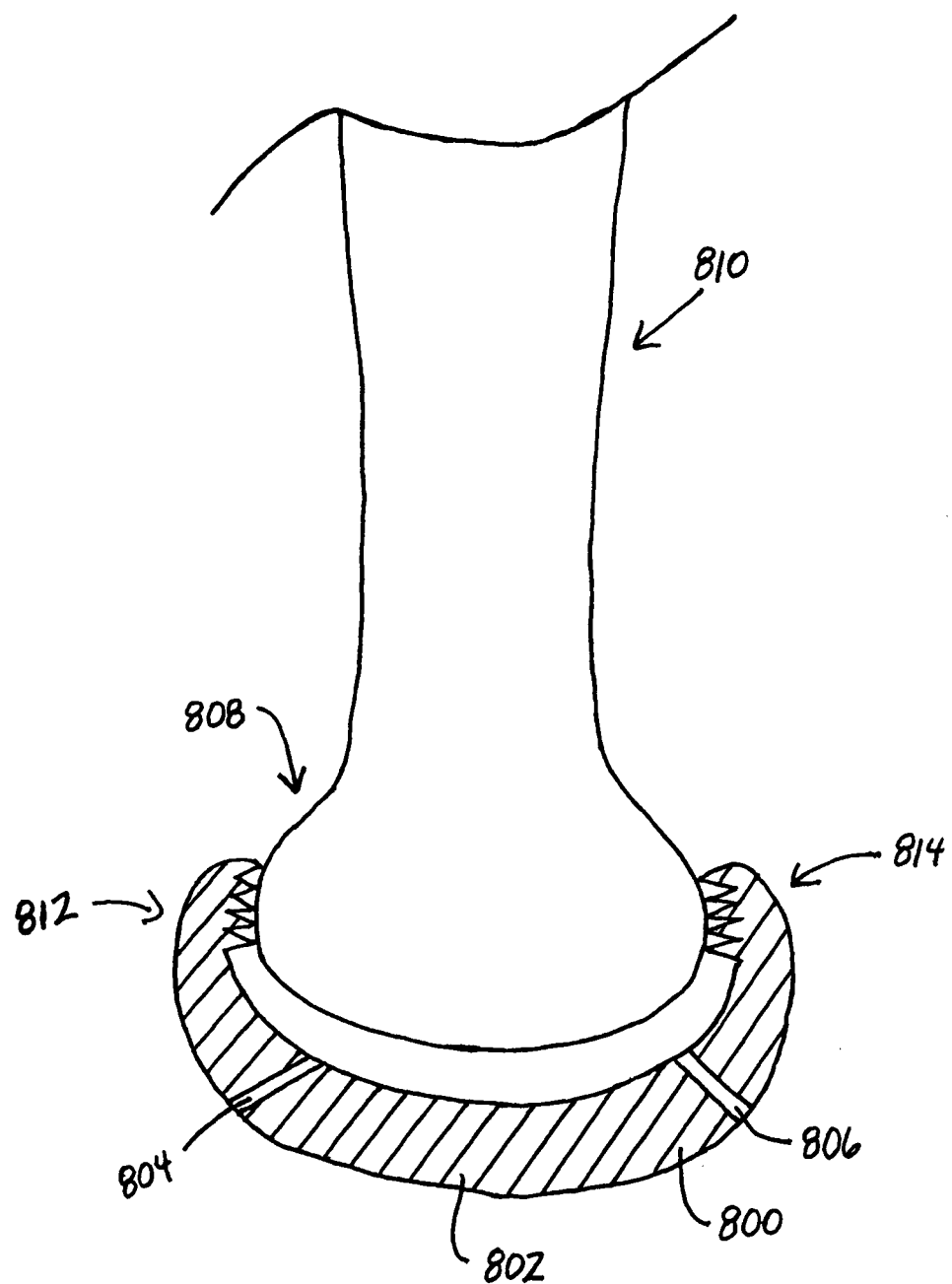
FIG. 8A is an illustration of an arthroplasty jig as the arthroplasty jig is being positioned on a portion of a femur of a subject.
Figure 8B:
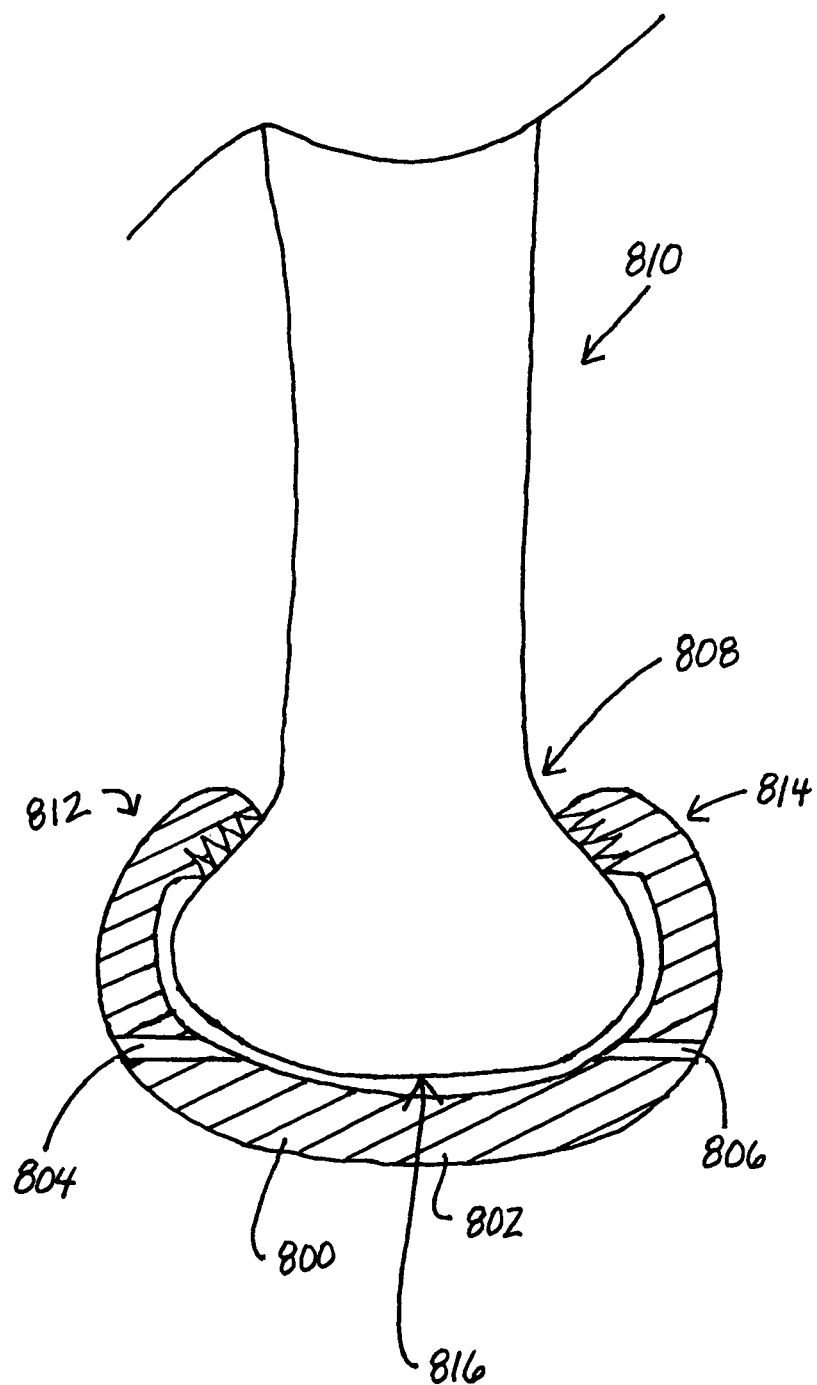
FIG. 8B is an illustration of the arthroplasty jig of FIG. 8A, after it has been aligned with the portion of the femur of FIG. 8A.

FIGS. 8A and 8B show another type of arthroplasty jig that may provide a tactile indication when correct alignment has been achieved at a target site. In FIG. 8A, an arthroplasty jig (800) including a jig body (802) having two slots (804) and (806) is being positioned on a distal end (808) of a femur (810). Jig body (802) may be formed of, for example, one or more shape-memory and/or superelastic materials that can allow the jig body to be temporarily deformed around the distal end of the femur. Jig body (802) also includes two claw-shaped positioning components (812) and (814). In FIG. 8B, arthroplasty jig (800) has been aligned with a surface (816) of femur (810). Claw-shaped positioning components (812) and (814) help to temporarily secure arthroplasty jig (800) to femur (810), which may thereby limit or prevent movement of the arthroplasty jig during an arthroplasty procedure. As arthroplasty jig (800) aligns with surface (816) of femur (810), a physician may sense arthroplasty jig (800) returning to its original configuration (i.e., its configuration prior to deformation), as well as claw-shaped positioning components (812) and (814) securing to femur (810). Furthermore, the physician may perceive that it is more difficult to move arthroplasty jig (800) once it has been aligned with surface (816) of femur (810).

Figure 9:
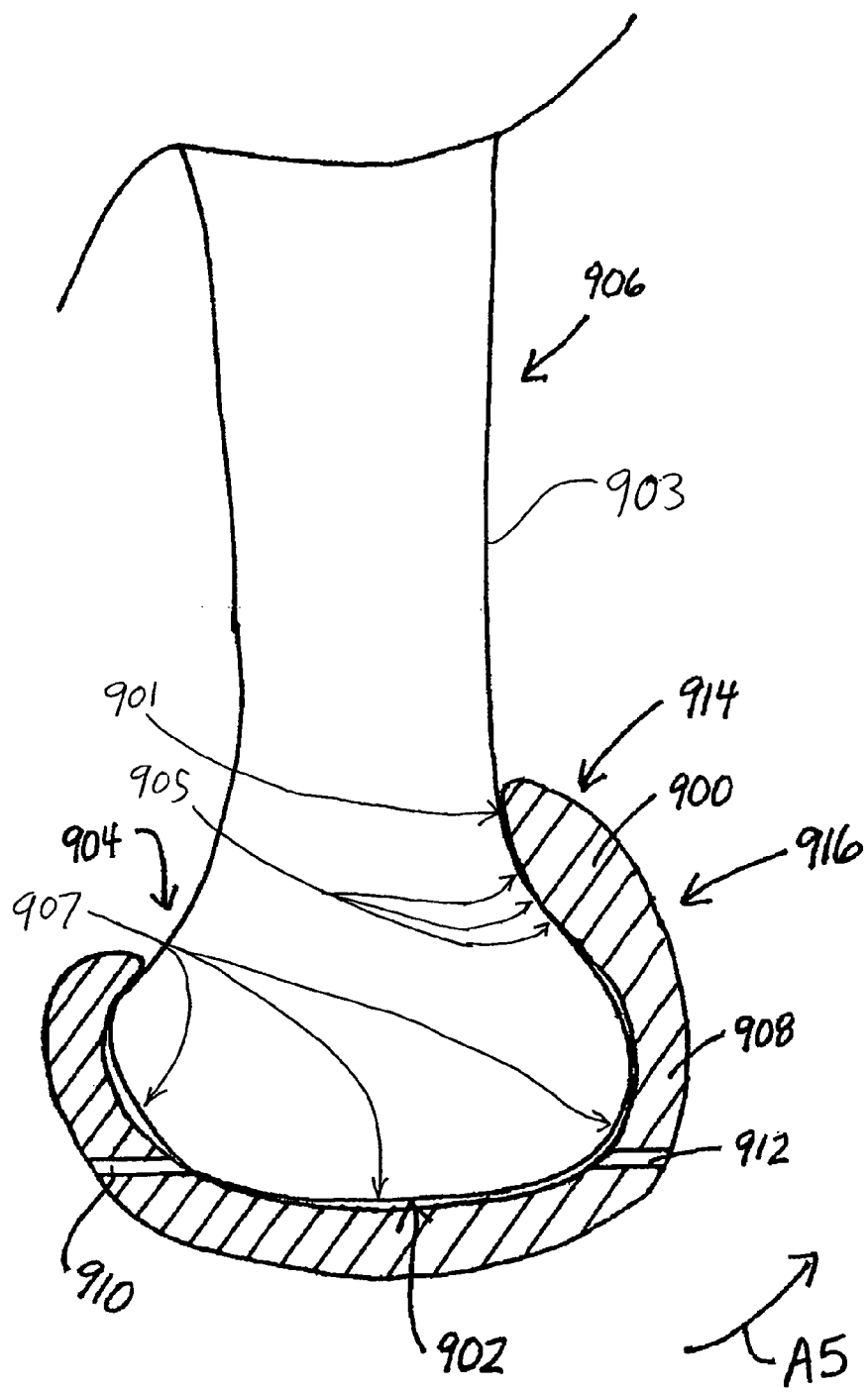
FIG. 9 is an illustration of a portion of a femur of a subject, and an arthroplasty jig aligned with the portion of the femur.

Certain variations of arthroplasty jigs may include one or more stops that help in the positioning and alignment of the arthroplasty jigs at a target site. For example, FIG. 9 shows an arthroplasty jig (900) that is aligned with a surface (902) of a distal end (904) of a femur (906). Arthroplasty jig (900) includes a jig body (908) with two slots (910) and (912), and a positioning component in the form of a stop (914) located at one of the ends (916) of jig body (908). The stop (914) may contact a femur surface, such as, for example, a surface (901) of the femur shaft (903) and a surface (905) for a transition region between the femoral shaft (903) and the condyle region (907) of the femoral distal end (904). As a physician is positioning arthroplasty jig (900) on femur (906), the physician may perceive contact between stop (914) and femur (906) when arthroplasty jig (900) becomes aligned with surface (902) of distal end (904) of femur (906). This tactile perception can provide an indication to the physician that alignment has been achieved, so that the physician no longer needs to adjust the position of the arthroplasty jig. Furthermore, the stop may even prevent the physician from further adjusting arthroplasty jig (900) in the direction of arrow (A5).

Figure 10A:
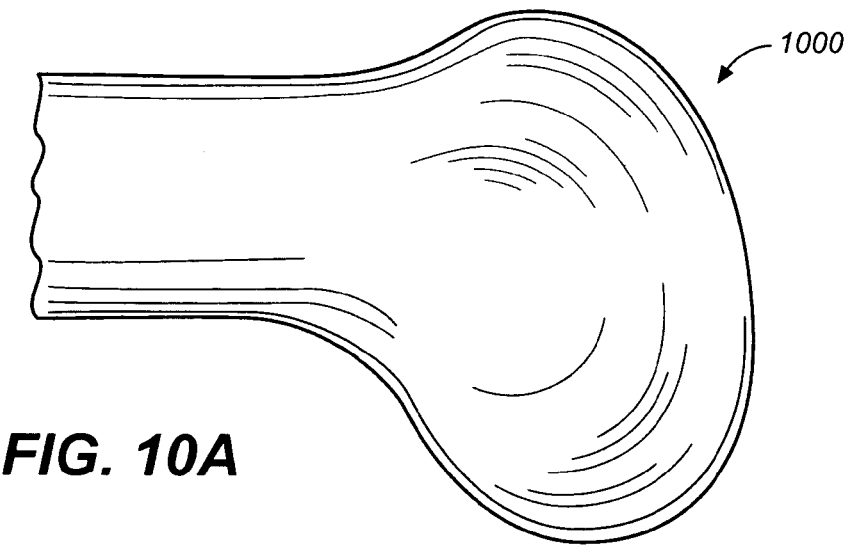
FIG. 10A is an illustration of a portion of a femur of a subject.
Figure 10B:
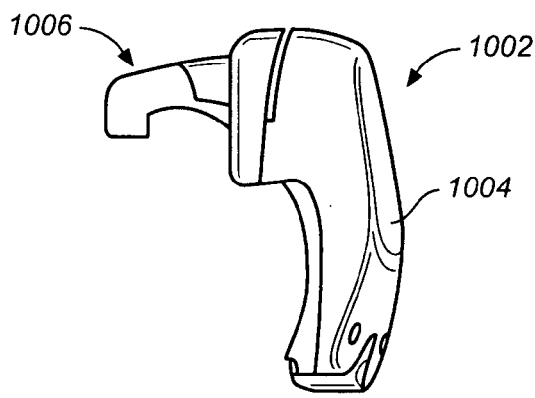
FIG. 10B is a front view of an arthroplasty jig.
Figure 10C:
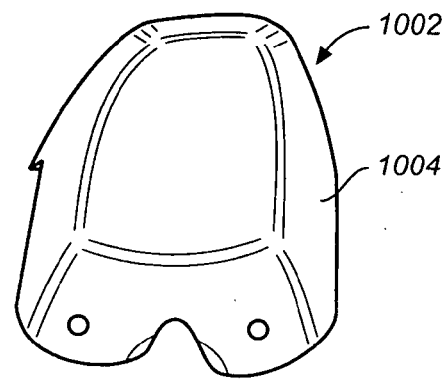
FIG. 10C is a side view of the arthroplasty jig of FIG. 10B.
Figure 10D:
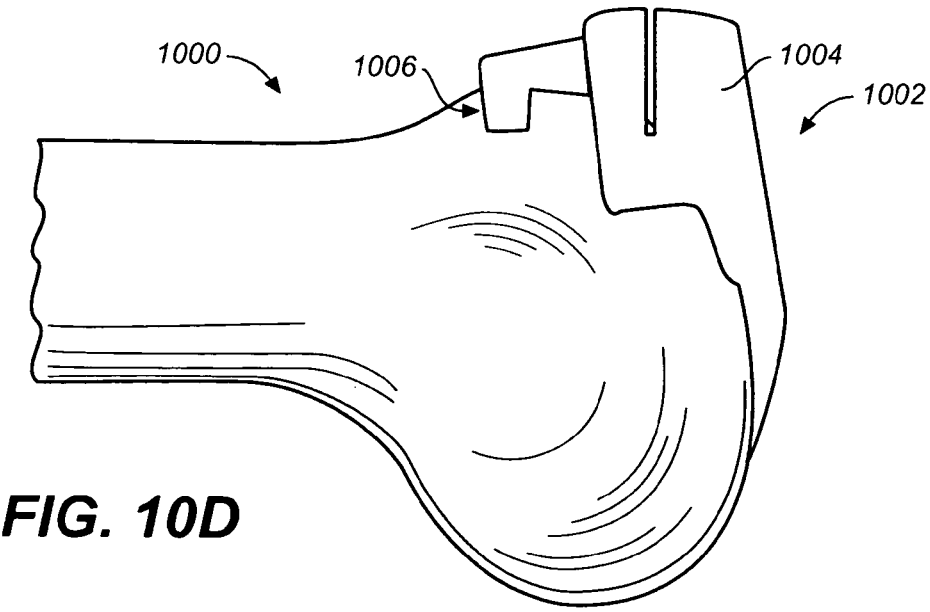
FIG. 10D is an illustration of the arthroplasty jig of FIGS. 10B and 10C, after it has been aligned with the portion of the femur of FIG. 10A.

In some variations, an arthroplasty jig may include one or more hook-shaped positioning components that can provide a tactile indication of proper positioning and alignment of the arthroplasty jig at a target site. For example, FIG. 10A shows a distal portion of a femur (1000), and FIGS. 10B and 10C show front and side views, respectively, of an arthroplasty jig (1002) configured for use with femur (1000). As shown in FIGS. 10B and 10C, arthroplasty jig (1002) includes a jig body (1004) and a hook-shaped positioning component (1006) extending from jig body (1004). As FIG. 10D shows, hook-shaped positioning component (1006) may be used to engage arthroplasty jig (1002) with femur (1000). For example, hook-shaped positioning component (1006) may be configured to temporarily latch onto one or more osteophytes on femur (1000), and/or to engage with cartilage.

While the above-described arthroplasty jigs are configured to provide a physician with a tactile indication of correct alignment, certain variations of arthroplasty jigs may alternatively or additionally provide one or more other types of indications of correct alignment. As an example, and as discussed above with reference to FIGS. 7A and 7B, an arthroplasty jig may provide an audible indication when its jig body has been properly positioned at a target site. While a snapping or locking sound has been described, in some variations, an arthroplasty jig may emit a different kind of sound. For example, in certain variations, an arthroplasty jig may include a sensor that, upon contacting a bone surface, triggers the emission of an audible signal, such as a temporary beeping sound. This beeping sound can be used to notify the physician that the arthroplasty jig has been properly positioned. As another example, and as discussed above with reference to FIGS. 3A and 3B, an arthroplasty jig may provide a visible indication when it has been properly positioned. An example of a visible indication is a flashing light, although other visual indications may be used. The visible indication may be activated by, for example, a sensor that has contacted a bone surface.

Figure 11A:
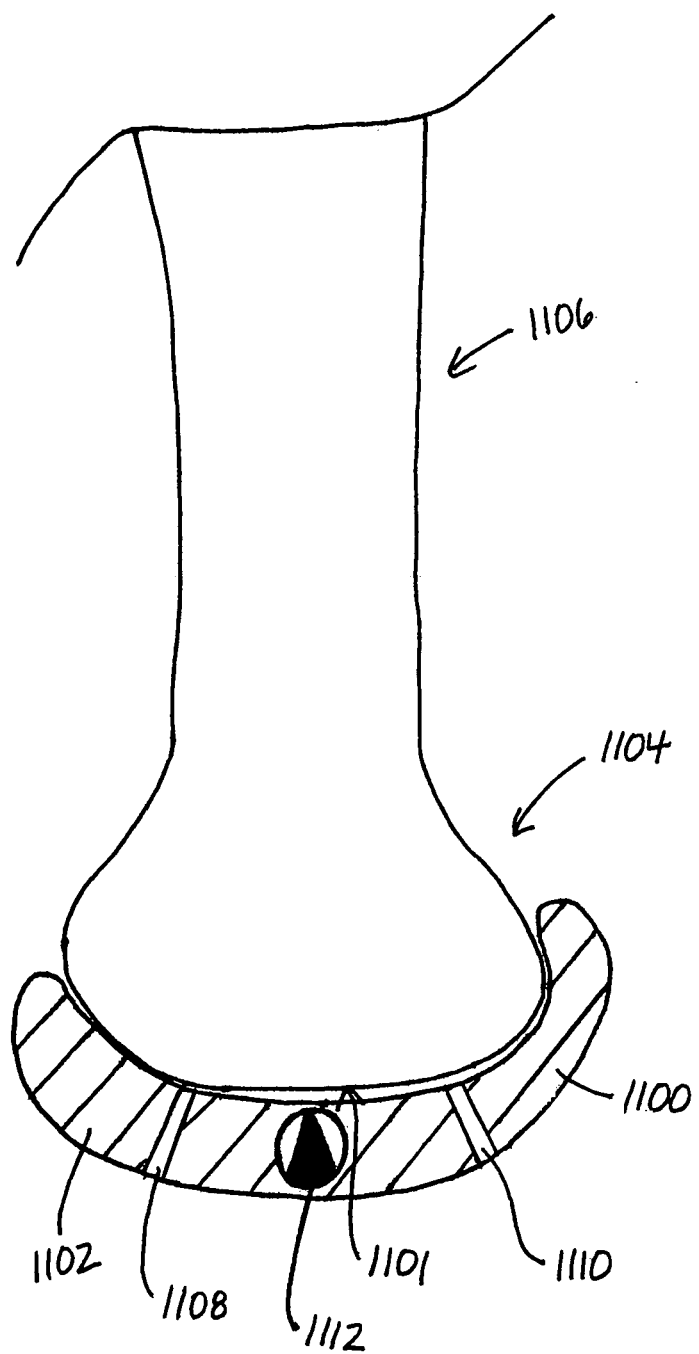
FIG. 11A is an illustration of a portion of a femur of a subject, and an arthroplasty jig aligned with the portion of the femur.
Figure 12:
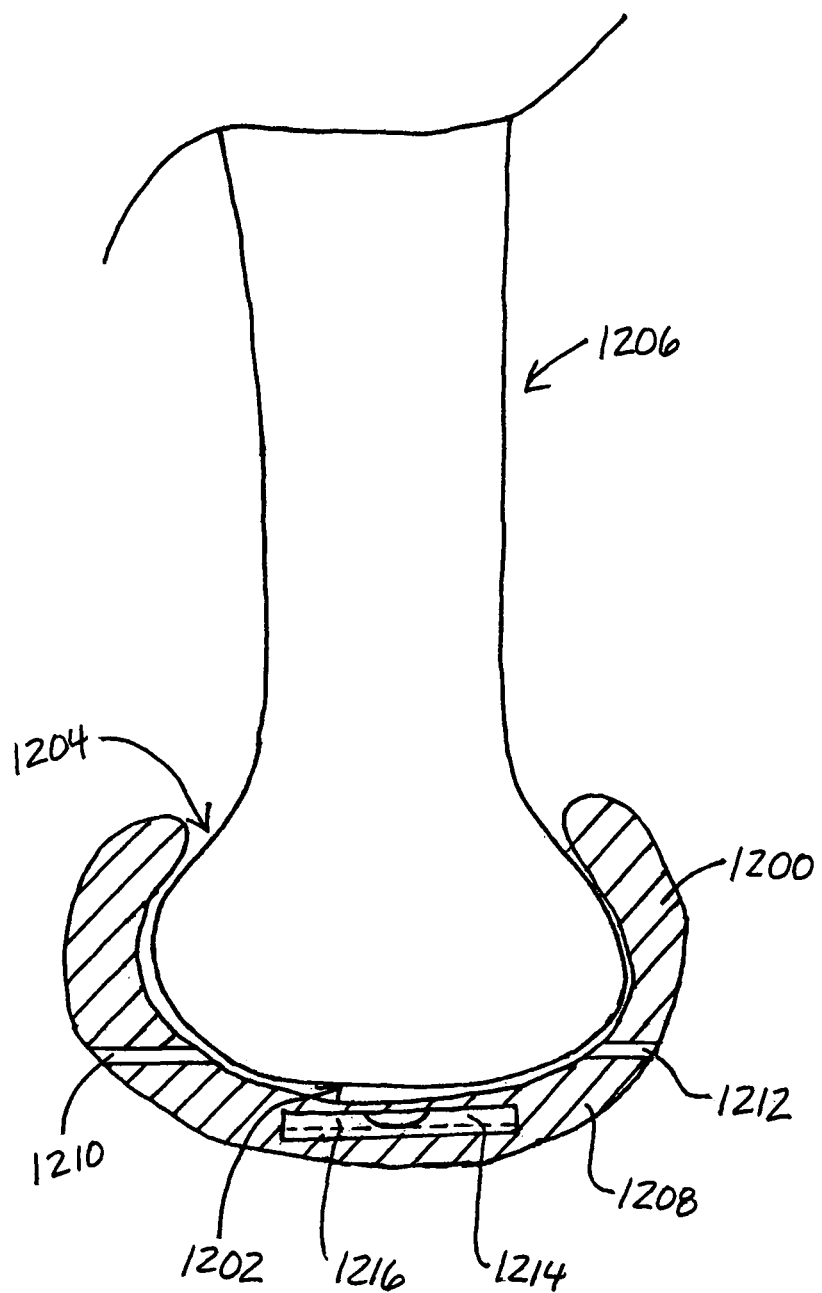
FIG. 12 is an illustration of a portion of a femur of a subject, and an arthroplasty jig aligned with the portion of the femur.

Additional examples of arthroplasty jigs that provide a visible indication of proper positioning and alignment are shown in FIGS. 11A-12. FIG. 11A shows an arthroplasty jig (1100) that is aligned with a surface (1101) of a distal end (1104) of a femur (1106). Arthroplasty jig (1100) includes a jig body (1102) with two slots (1108) and (1110) and an alignment indicator (1112). Because arthroplasty jig (1100) is properly aligned with surface (1101) in FIG. 11 A, alignment indicator (1112) displays a full black triangle. However, and as shown in FIG. 11B, when arthroplasty jig (1100) is not properly aligned with surface (1101), the triangle in alignment indicator (1112) is no longer entirely black but rather, a combination of black and white (or another color). Alignment indicator (1112) may be formed of, for example, a black plate and a white plate that can shift into different positions relative to each other, depending on the position of arthroplasty jig (1100). FIG. 12 shows an arthroplasty jig (1200) that is aligned with a surface (1202) of a distal end (1204) of a femur (1206). Arthroplasty jig (1200) includes a jig body (1208) having two slots (1210) and (1212), and a level (1214). Because arthroplasty jig (1200) is aligned with surface (1202), the fluid (1216) in level (1214) indicates that the arthroplasty jig is level. However, if arthroplasty jig (1200) were not aligned with surface (1202), then the fluid would indicate that the arthroplasty jig was not level.

As discussed above, other methods of correctly identifying an arthroplasty jig and positioning the arthroplasty jig at a target site may be used, either in conjunction with one or more of the above-described methods, or as an alternative to one or more of the above-described methods.

One example of such a method is the inclusion of identifying information on an arthroplasty jig. The presence of the identifying information on the arthroplasty jig may reduce the likelihood of the wrong arthroplasty jig being selected for use during a particular arthroplasty procedure. In some variations, the presence of identifying information on an arthroplasty jig may result in reduced procedure time. For example, it may allow a physician to readily confirm that the correct arthroplasty jig has been selected for a particular patient or procedure.

The identifying information may include any type of information that is useful on a medical device. For example, the identifying information may include patient data (e.g., a patient's name, date of birth, weight, height, allergies, etc.), doctor information, surgery information (e.g., date of surgery, hospital at which surgery is to take place, etc.), information regarding the size and/or materials of the jig body, company logos, barcodes, etc. In some variations, the identifying information may provide specific information about a target site, and/or may help a physician to position the arthroplasty jig. For example, the arthroplasty jig may include markings such as "femur," "tibia," "left knee," "right knee," "this side up," "this side down," and/or any other appropriate markings. In certain variations, an arthroplasty jig may include markings that provide one or more of the dimensions of the arthroplasty jig, such as the length, width, or thickness of the arthroplasty jig. Other examples of markings may include markings that help a physician to make measurements, such as millimeter markings. Any number of different markings may be used on an arthroplasty jig, and the examples provided here are not intended to be limiting.

Identifying information may be added onto a jig body in any of a number of different ways. For example, the identifying information may be printed onto, and/or engraved (e.g., etched, cut, or carved) into, the jig body, and/or may be located on one or more adhesive labels that are affixed to the jig body. Any other methods of marking an arthroplasty jig with one or more biocompatible markings may also be used. An arthroplasty jig may include just one marking, or multiple markings. The markings may be the same color or different colors, and may be in the same font or different fonts. Furthermore, while arthroplasty jigs that are marked with identifying information have been described, certain variations of arthroplasty jigs may include other types of markings. As an example, certain variations of arthroplasty jigs may include aesthetic markings, such as designs.

In some variations, identifying information may be provided on a tag (e.g., a metal tag) that is temporarily attached to the arthroplasty jig. The identifying information may, for example, be engraved into the tag. The arthroplasty jig itself may or may not also be marked with identifying information. The metal tag may be removed (e.g., by a physician) prior to the arthroplasty jig being used in an arthroplasty procedure.

Figure 13:
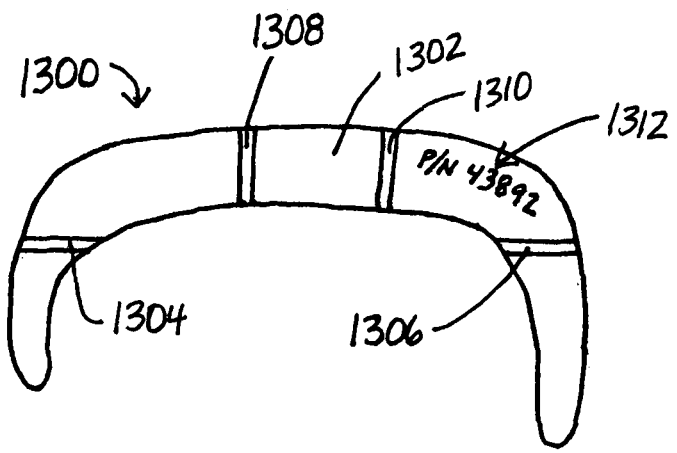
FIG. 13 is an illustration of an arthroplasty jig.
Figure 14:
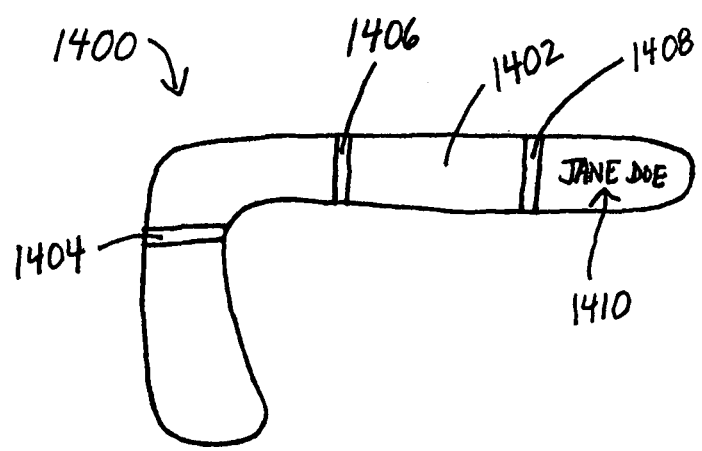
FIG. 14 is an illustration of an arthroplasty jig.

FIGS. 13 and 14 show examples of arthroplasty jigs that are marked with identifying information. As shown in FIG. 13, a femoral arthroplasty jig (1300) includes a jig body (1302) having two slots (1304) and (1306) and two apertures (1308) and (1310). Identifying information (1312) (as shown, a part number) is marked on jig body (1302). Similarly, FIG. 14 shows a tibial arthroplasty jig (1400) including a jig body (1402) having a slot (1404) and two apertures (1406) and (1408). Jig body (1402) is marked with identifying information (1410) (as shown, a patient name).

Arthroplasty jigs may be formed using any of a number of different procedures. In some variations, arthroplasty jigs may be formed from one or more arthroplasty jig blanks. The arthroplasty jig blanks that are used to form arthroplasty jigs may have different sizes and/or shapes. For example, some arthroplasty jig blanks may be designed for use with the left side of a patient's body (e.g., a left knee), while other arthroplasty jig blanks are designed for use with the right side of a patient's body (e.g., the right knee). In certain variations, an arthroplasty jig blank may be marked (e.g., using one or more of the marking methods described above with reference to arthroplasty jigs).

The arthroplasty jigs and jig blanks described herein may be formed of any of a number of different materials. They may be formed of just one material, or multiple materials, such as a blend of different materials or layers of different materials. Examples of suitable materials include polymers, metals, ceramics, metal alloys, and combinations thereof. Specific examples of polymers include acetal resins (e.g., Delrin®), polyetheretherketones (PEEK), polycarbonates, polyamides, polyesters, polystyrenes, polyacrylates, vinyl polymers, and polyurethanes. Specific examples of metals and metal alloys include gold, platinum, palladium, stainless steel, cobalt alloys (e.g., Elgiloy®), and nickel-titanium alloys (e.g., Nitinol™). In some variations, the arthroplasty jig blanks may be formed of one or more plastics. In such variations, the blanks may be formed, for example, using injection molding technology and/or thermal plastic press forming technology. In certain variations, an arthroplasty jig may be intended to be disposable, while in other variations, an arthroplasty jig may be intended to be reusable. The materials out of which an arthroplasty jig is formed may be selected with these and/or other criteria in mind. Moreover, certain variations of arthroplasty jigs may be formed of two or more layers of different materials, and/or may include one or more coatings.

In some variations, arthroplasty jigs may be customized so that the accuracy of their positioning and alignment (and, therefore, the accuracy with which they position and align instruments) may be enhanced. Various methods may be used to form customized arthroplasty jigs, such as the methods described, for example, in U.S. patent application Ser. No. 10/146,862, filed on May 15, 2002, which is hereby incorporated by reference in its entirety.

Figure 15:
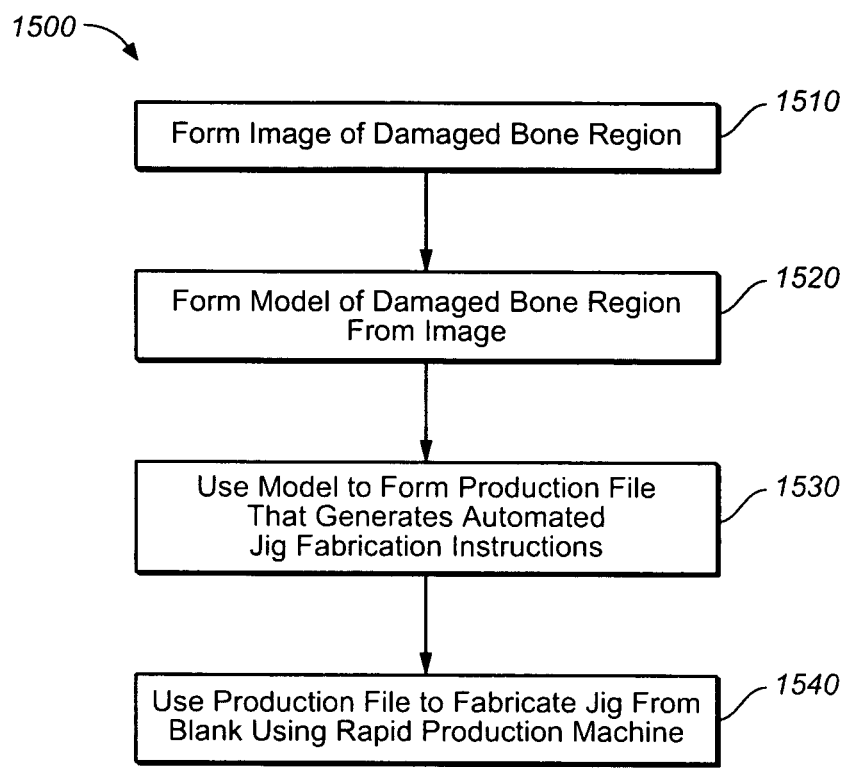
FIG. 15 is a flowchart representation of a method of forming an arthroplasty jig.

One variation of a method (1500) that may be used to form customized arthroplasty jigs is depicted as a flowchart in FIG. 15. As shown in FIG. 15, this illustrative method comprises forming an image of a damaged bone region of a patient (1510) using, for example, computer tomography (CT) and/or magnetic resonance imaging (MRI). The image may be formed specifically of the damaged bone region, or may include portions of the bone that are not damaged. As an example, an image of a damaged knee region may include the entirety of the knee region, as well as the entirety of the associated femur and tibia. After the image has been formed, a three-dimensional model of the damaged bone region is formed from the image (1520). The model may be formed, for example, by using the image to determine location coordinate values of each of a sequence of spaced apart surface points in the damaged bone region, and then using a mathematical model to estimate or compute the three-dimensional model. Thereafter, the model and the image are used to generate a production file that provides automated arthroplasty jig fabrication instructions (1530) to a rapid production machine. The rapid production machine then fabricates a customized arthroplasty jig from an arthroplasty jig blank according to the instructions (1540).

While one method of manufacturing a customized arthroplasty jig has been described above, other methods may be used. For example, one-, two-, and three-dimensional measurements of a target site may be taken using lasers, electromagnetic or optical tracking systems, or other imaging methods. As an example, while CT and MRI have been described, other imaging methods that may be used include X-ray technology, optical coherence tomography, ultrasound imaging, and optical imaging. In some variations, multiple imaging techniques may be used together to image a target site. Moreover, the measurements that are used to image an area may be taken in a non-invasive manner, or may be taken intra-operatively (e.g., using optical, mechanical, and/or ultrasound probes). Additionally, while customized arthroplasty jigs have been described, some variations of arthroplasty jigs may not be customized for a particular patient.

While methods and devices described herein have been described with respect to arthroplasty jigs, in some variations, one or more features of the methods and devices described above may be applied to implants, such as arthroplasty implants. Moreover, while arthroplasty procedures have been described, the jigs and implants described herein may be used in any of a number of different procedures, including, for example, spinal surgery.

While the methods, devices, and apparatuses have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the pending claims.

What is claimed is:

1. A customized arthroplasty jig for facilitating an arthroplasty procedure on a bone of a patient, the bone having a joint region and a shaft extending away from the joint region, the joint region having an associated surface of at least one of cartilage or bone, the jig comprising:
   a curvilinear jig surface configured to at least one of align with or position on the associated surface in a customized fashion, the curvilinear jig surface manufactured in a customized configuration particular to the associated surface of the patient; and a positioning component being of a fixed unitary construction with the curvilinear jig surface and configured to contact the shaft when the curvilinear jig surface at least one of aligns with or positions on the associated surface in the customized fashion.

2. A customized arthroplasty jig for facilitating an arthroplasty procedure on a bone of a patient, the bone having a joint region, a shaft extending away from the joint region and a transition region between the joint region and the shaft, the joint region having an associated surface of at least one of cartilage or bone, the jig comprising:

a curvilinear jig surface configured to at least one of align with or position on the associated surface in a customized fashion, the curvilinear jig surface manufactured in a customized configuration particular to the associated surface of the patient; and a positioning component being of a fixed unitary construction with the curvilinear jig surface and configured to contact the transition region when the curvilinear jig surface at least one of aligns with or positions on the associated surface in the customized fashion.

3. The jig as in any of claims 1 or 2, in which the joint region includes at least one femoral condyle.

4. The jig as in any of claims 1 or 2, in which the joint region includes at least one tibia plateau.

5. The jig as in any of claims 1 or 2, in which the curvilinear jig surface is at least a result of a manufacturing process including: forming at least one image of the joint region; forming a three-dimensional model of the joint region from the at least one image; and generating the jig surface based at least in part on data determined from the three-dimensional model.

6. The jig of claim 5, wherein the at least one image is generated via at least one of MRI or CT.

7. The jig according to claims 1 or 2, further comprising at least one of a cutting instrument guide, a drilling instrument guide or a pin delivery guide.

8. The jig as in any of claims 1 or 2, in which the positioning component generally terminates in a contact-making free end including at least one of a pointed configuration or a rounded configuration.

9. The jig as in any of claims 1 or 2, in which the arthroplasty jig includes identifying information present on a jig body of the arthroplasty jig, the identifying information associated with at least one of the patient or a medical professional.

10. The jig of claim 9, wherein the identifying information is engraved into the jig body.

11. The jig of claim 9, wherein the identifying information is printed onto the jig body.

12. The jig of claim 9, wherein the identifying information is provided on a label that is affixed to the jig body.

13. The jig of claim 9, wherein the identifying information includes at least one of a patient name, a number associated with the patient, an identification of the bone, or an identification of the joint region.

14. The jig as in any of claims 1 or 2, in which the bone is that of a femur.

15. The jig of claim 14, wherein the joint region is a knee region.

16. The jig as in any of claims 1 or 2, in which the bone is that of a tibia.

17. The jig of claim 16, wherein the joint region is a knee region.

* * * * *